United States Patent
Spenser et al.

(10) Patent No.: US 6,893,460 B2
(45) Date of Patent: May 17, 2005

(54) IMPLANTABLE PROSTHETIC VALVE

(75) Inventors: Benjamin Spenser, Caesarea (IL);
Netanel Benichu, Nir Etzion (IL);
Assaf Bash, Givat Ada (IL); Avraham Zakai, Zichron Yaacov (IL)

(73) Assignee: Percutaneous Valve Technologies Inc., Irvine, CA (US)

( * ) Notice: Subject to any disclaimer, the term of this patent is extended or adjusted under 35 U.S.C. 154(b) by 0 days.

(21) Appl. No.: 09/975,750

(22) Filed: Oct. 11, 2001

(65) Prior Publication Data

US 2003/0153974 A1 Aug. 14, 2003

(51) Int. Cl.⁷ .................................................. A61F 2/06
(52) U.S. Cl. ........................................................ 623/2.14
(58) Field of Search ........................... 623/2.14, 2.15, 623/2.17, 2.18, 2.19, 2.12, 2.13, 2.1

(56) References Cited

U.S. PATENT DOCUMENTS

| | | |
|---|---|---|
| 3,548,417 A | 12/1970 | Kisher |
| 3,657,744 A | 4/1972 | Ersek |
| 4,265,694 A | 5/1981 | Boretos et al. |
| 4,345,340 A * | 8/1982 | Rosen ........................ 623/2.19 |
| 4,373,216 A | 2/1983 | Klawitter |
| 4,406,022 A | 9/1983 | Roy |
| 4,535,483 A | 8/1985 | Klawitter et al. |
| 4,605,407 A | 8/1986 | Black et al. |
| 4,643,732 A | 2/1987 | Pietsch et al. |
| 4,692,164 A | 9/1987 | Dzemeshkevich et al. |
| 4,759,758 A | 7/1988 | Gabbay |
| 4,829,990 A | 5/1989 | Thuroff et al. |
| 4,851,001 A | 7/1989 | Taheri |
| 5,032,128 A | 7/1991 | Alonso |
| 5,037,434 A | 8/1991 | Lane |
| 5,080,668 A | 1/1992 | Bolz et al. |
| 5,282,847 A | 2/1994 | Trescony et al |
| 5,360,444 A | 11/1994 | Kusuhara . |
| 5,411,552 A | 5/1995 | Andersen et al. |
| 5,500,014 A | 3/1996 | Quijano et al. |
| 5,545,214 A | 8/1996 | Stevens |
| 5,571,175 A | 11/1996 | Vanney et al. |
| 5,591,195 A | 1/1997 | Taheri et al. |
| 5,607,464 A | 3/1997 | Trescony et al. |
| 5,609,626 A | 3/1997 | Quijano et al. |
| 5,728,068 A | 3/1998 | Leone et al. |
| 5,749,890 A | 5/1998 | Shaknovich |
| 5,840,081 A | 11/1998 | Andersen et al. |
| 5,855,601 A | 1/1999 | Bessler et al. |
| 5,855,602 A | 1/1999 | Angell |
| 6,132,473 A | 10/2000 | Williams et al. |
| 6,171,335 B1 * | 1/2001 | Wheatley et al. .......... 623/2.17 |
| 6,454,799 B1 | 9/2002 | Schreck |
| 6,458,153 B1 | 10/2002 | Bailey et al. |
| 6,468,660 B2 * | 10/2002 | Ogle et al. ................... 428/413 |

* cited by examiner

Primary Examiner—Corrine McDermott
Assistant Examiner—William H Matthews
(74) Attorney, Agent, or Firm—David L. Hauser; William H. Dippert

(57) ABSTRACT

A valve prosthesis device is disclosed suitable for implantation in body ducts. The device comprises support stent, comprised of a deployable construction adapted to be initially crimped in a narrow configuration suitable for catheterization through the body duct to a target location and adapted to be deployed by exerting substantially radial forces from within by means of a deployment device to a deployed state in the target location, the support stent provided with a plurality of longitudinally rigid support beams of fixed length; valve assembly comprising a flexible conduit having an inlet end and an outlet, made of pliant material attached to the support beams providing collapsible slack portions of the conduit at the outlet. When flow is allowed to pass through the valve prosthesis device from the inlet to the outlet the valve assembly is kept in an open position, whereas a reverse flow is prevented as the collapsible slack portions of the valve assembly collapse inwardly providing blockage to the reverse flow.

31 Claims, 25 Drawing Sheets

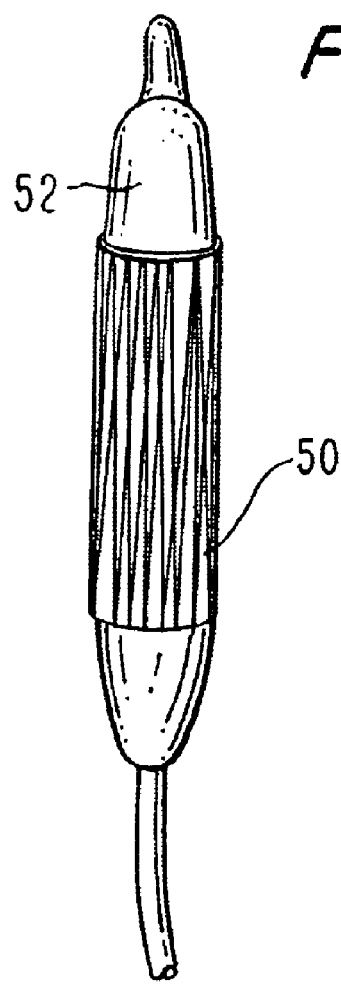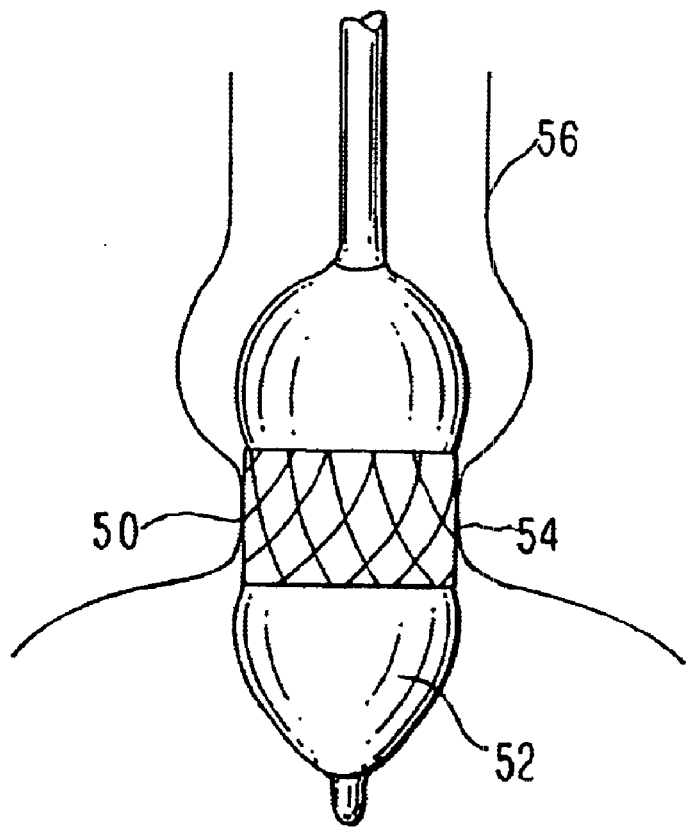

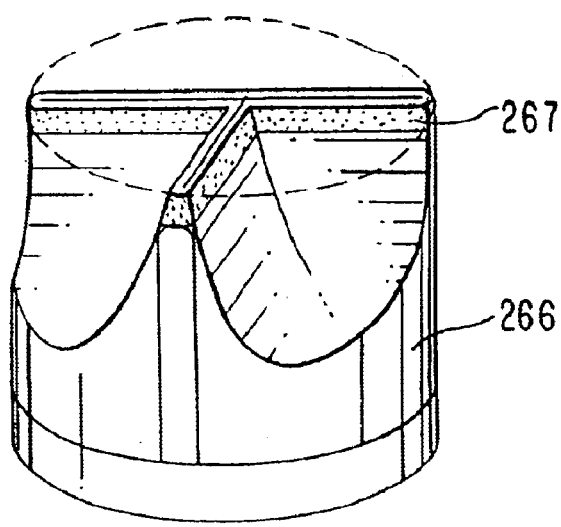
FIG. 15a
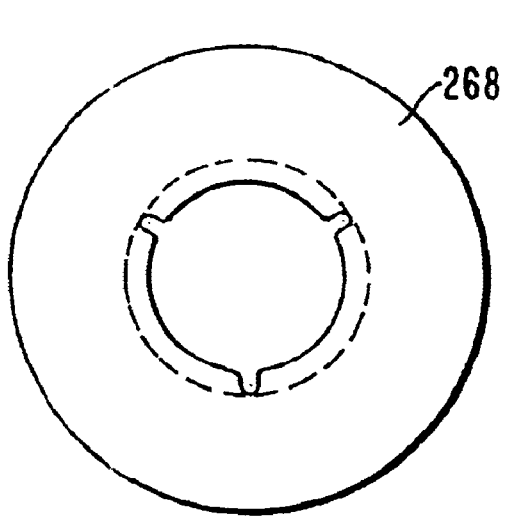 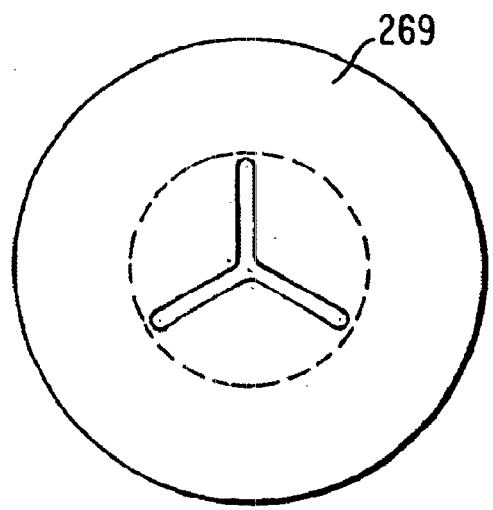
FIG. 15b                FIG. 15c

IMPLANTABLE PROSTHETIC VALVE

FIELD OF THE INVENTION

The present invention relates to implantable devices. More particularly, it relates to a valve prosthesis for cardiac implantation or for implantation in other body ducts.

BACKGROUND OF THE INVENTION

There are several known prosthesis valves that have been previously described. U.S. Pat. No. 5,411,552 (Andersen et al.), entitled VALVE PROSTHESIS FOR IMPLANTATION IN THE BODY AND CATHETER FOR IMPLANTING SUCH VALVE PROSTHESIS, discloses a valve prosthesis comprising a stent made from an expandable cylinder-shaped thread structure comprising several spaced apices. The elastically collapsible valve is mounted on the stent with the commissural points of the valve secured to the projecting apices, which prevents the valve from turning inside out. Deployment of the valve can be achieved by using an inflatable balloon which in its deflated state is used to carry about it the valve structure to its position and, when inflated, deploys the stent in position to its final size. See, also, U.S. Pat. No. 6,168,614 (Andersen et al.) entitled VALVE PROSTHESIS FOR IMPLANTATION IN THE BODY and U.S. Pat. No. 5,840,081 (Andersen et al.), titled SYSTEM AND METHOD FORIMPLANTING CARDIAC VALVES.

In PCT/EP97/07337 (Letac, Cribier et al.), published as WO 98/29057, entitled VALVE PROSTHESIS FOR IMPLANTATION IN BODY CHANNELS, there is disclosed a valve prosthesis comprising a collapsible valve structure and an expandable frame on which the valve structure is mounted. The valve structure is composed of a valvular tissue compatible with the human body and blood, the valvular tissue being sufficiently supple and resistant to allow the valve structure to be deformed from a closed state to an opened state. The valvular tissue forms a continuous surface and is provided with guiding means formed or incorporated within, the guiding means creating stiffened zones which induce the valve structure to follow a patterned movement in its expansion to its opened state and in its turning back to its closed state. The valve structure can be extended to an internal cover which is fastened to the lower part of the valve structure to prevent regurgitation.

There are several known methods currently used for replacing aortic valves and several types of artificial prosthetic devices. Mechanical valves are commonly used in several different designs (single and double flap) manufactured by well-known companies such as St. Jude, Medtronic, Sulzer, and others. Some of the main disadvantages of these devices are: a need for permanent treatment of anticoagulants, noisy operation, and a need for a large-scale operation to implant.

There is a wide range of biologically based valves made of natural valves or composed of biological materials such as pericardial tissue. These too are made and marketed by well-known companies such as Edwards Lifesciences, Medtronic, Sulzer, Sorin, and others.

Polymer valves are new and are not yet in use, but several companies are in the process of developing such products. A new type of prosthesis is being considered, based on artificial polymer materials such as polyurethane.

The present invention introduces several novel structural designs for implantable valves. An aspect of the present invention deals with the possibility of implanting the valve percutaneously, i.e., inserting the valve assembly on a delivery device similar to a catheter, then implanting the valve at the desired location via a large blood vessel such as the femoral artery, in a procedure similar to other known interventional cardiovascular procedures. The percutaneous deployment procedure and device has an impact on the product design in several parameters, some of which are explained hereinafter.

The percutaneous implantation of medical devices, and particularly prosthetic valves, is a preferred surgical procedure for it involves making a very small perforation in the patient's skin (usually in the groin or armpit area) under local anesthetic sedation, as opposed to a large chest surgery incision, which requires general anesthesia, opening a large portion of the chest, and cardiopulmonary bypass. This percutaneous procedure is therefore considered safer.

The present invention provides a series of new concepts in the field of aortic valves and other human valves.

SUMMARY OF THE INVENTION

It is therefore thus provided, in accordance with a preferred embodiment of the present invention, a valve prosthesis device suitable for implantation in body ducts, the device comprising:

a support stent, comprised of a deployable construction adapted to be initially crimped in a narrow configuration suitable for catheterization through the body duct to a target location and adapted to be deployed by exerting substantially radial forces from within by means of a deployment device to a deployed state in the target location, the support stent provided with a plurality of longitudinally rigid support beams of fixed length; and a valve assembly comprising a flexible conduit having an inlet end and an outlet, made of pliant material attached to the support beams providing collapsible slack portions of the conduit at the outlet, whereby when flow is allowed to pass through the valve prosthesis device from the inlet to the outlet the valve assembly is kept in an open position, whereas a reverse flow is prevented as the collapsible slack portions of the valve assembly collapse inwardly providing blockage to the reverse flow.

Furthermore, in accordance with another preferred embodiment of the present invention, the support stent comprises an annular frame.

Furthermore, in accordance with another preferred embodiment of the present invention, said valve assembly has a tricuspid configuration.

Furthermore, in accordance with another preferred embodiment of the present invention, said valve assembly is made from biocompatible material.

Furthermore, in accordance with another preferred embodiment of the present invention, the valve assembly is made from pericardial tissue, or other biological tissue.

Furthermore, in accordance with another preferred embodiment of the present invention, said valve assembly is made from biocompatible polymers.

Furthermore, in accordance with another preferred embodiment of the present invention, the valve assembly is made from materials selected from the group consisting of polyurethane and polyethylene terphthalane.

Furthermore, in accordance with another preferred embodiment of the present invention, said valve assembly comprises a main body made from polyethylene terphthalane and leaflets made from polyurethane.

Furthermore, in accordance with another preferred embodiment of the present invention, said support stent is made from nickel titanium.

Furthermore, in accordance with another preferred embodiment of the present invention, the support beams are substantially equidistant and substantially parallel so as to provide anchorage for the valve assembly.

Furthermore, in accordance with another preferred embodiment of the present invention, the support beams are provided with bores so as to allow stitching or tying of the valve assembly to the beams.

Furthermore, in accordance with another preferred embodiment of the present invention, the support beams are chemically adhered to the support stent.

Furthermore, in accordance with another preferred embodiment of the present invention, said valve assembly is riveted to the support beams.

Furthermore, in accordance with another preferred embodiment of the present invention, said valve assembly is stitched to the support beams.

Furthermore, in accordance with another preferred embodiment of the present invention, said beams are manufactured by injection using a mold, or by machining.

Furthermore, in accordance with another preferred embodiment of the present invention, said valve assembly is rolled over the support stent at the inlet.

Furthermore, in accordance with another preferred embodiment of the present invention, said valve device is manufactured using forging or dipping techniques.

Furthermore, in accordance with another preferred embodiment of the present invention, said valve assembly leaflets are longer than needed to exactly close the outlet, thus when they are in the collapsed state substantial portions of the leaflets fall on each other creating better sealing.

Furthermore, in accordance with another preferred embodiment of the present invention, said valve assembly is made from coils of a polymer, coated by a coating layer of same polymer.

Furthermore, in accordance with another preferred embodiment of the present invention, said polymer is polyurethane.

Furthermore, in accordance with another preferred embodiment of the present invention, the support stent is provided with heavy metal markers so as to enable tracking and determining the valve device position and orientation.

Furthermore, in accordance with another preferred embodiment of the present invention, the heavy metal markers are selected from gold, platinum, iridium, or tantalum.

Furthermore, in accordance with another preferred embodiment of the present invention, the valve assembly leaflets are provided with radio-opaque material at the outlet, so as to help tracking the valve device operation in vivo.

Furthermore, in accordance with another preferred embodiment of the present invention, said radio-opaque material comprises gold thread.

Furthermore, in accordance with another preferred embodiment of the present invention, the diameter of said support stent, when fully deployed is in the range of from about 19 to about 25 mm.

Furthermore, in accordance with another preferred embodiment of the present invention, the diameter of said support stent may be expanded from about 4 to about 25 mm.

Furthermore, in accordance with another preferred embodiment of the present invention, the support beams are provided with bores and wherein the valve assembly is attached to the support beams by means of U-shaped rigid members that are fastened to the valve assembly and that are provided with extruding portions that fit into matching bores on the support beams.

Furthermore, in accordance with another preferred embodiment of the present invention, the support beams comprise rigid support beams in the form of frame construction, and the valve assembly pliant material is inserted through a gap in the frame and a fastening rod is inserted through a pocket formed between the pliant material and the frame and holds the valve in position.

Furthermore, in accordance with another preferred embodiment of the present invention, the main body of the valve assembly is made from coiled wire coated with coating material.

Furthermore, in accordance with another preferred embodiment of the present invention, the coiled wire and the coating material is made from polyurethane.

Furthermore, in accordance with another preferred embodiment of the present invention, a strengthening wire is interlaced in the valve assembly at the outlet of the conduit so as to define a fault line about which the collapsible slack portion of the valve assembly may flap.

Furthermore, in accordance with another preferred embodiment of the present invention, the strengthening wire is made from nickel titanium alloy.

Furthermore, in accordance with another preferred embodiment of the present invention, there is provided a valve prosthesis device suitable for implantation in body ducts, the device comprising a main conduit body having an inlet and an outlet and pliant leaflets attached at the outlet so that when a flow passes through the conduit from the inlet to the outlet the leaflets are in an open position allowing the flow to exit the outlet, and when the flow is reversed the leaflets collapse so as to block the outlet, wherein the main body is made from polyethylene terphtalate and collapsible leaflets are made form polyurethane.

Furthermore, in accordance with another preferred embodiment of the present invention, support beams made from polyurethane are provided on the main body and wherein the leaflets are attached to the main body at the support beams.

Furthermore, in accordance with another preferred embodiment of the present invention, said support beams are chemically adhered to the main body.

Furthermore, in accordance with another preferred embodiment of the present invention, there is provided a valve prosthesis device suitable for implantation in body ducts, the device comprising:

a support stent, comprised of a deployable construction adapted to be initially crimped in a narrow configuration suitable for catheterization through the body duct to a target location and adapted to be deployed by exerting substantially radial forces from within by means of a deployment device to a deployed state in the target location, the support stent provided with a plurality of longitudinally rigid support beams of fixed length;

a valve assembly comprising a flexible conduit having an inlet end and an outlet, made of pliant material attached to the support beams providing collapsible slack portions of the conduit at the outlet; and substantially equidistant rigid support beams interlaced or attached to the slack portion of the valve assembly material, arranged longitudinally.

Furthermore, in accordance with another preferred embodiment of the present invention, there is provided a crimping device for crimping the valve device described above or in claim 1, the crimping device comprising a plurality of adjustable plates that resemble a typical SLR (Single Lens Reflex) camera variable restrictor, each provided with a blade, that are equally dispersed in a radial symmetry but each plate moves along a line passing off an opening in the center, all plates equidistant from that center opening.

Furthermore, in accordance with another preferred embodiment of the present invention, the multiple plates are adapted to move simultaneously by means of a lever and transmission.

Furthermore, in accordance with another preferred embodiment of the present invention, there is provided a method for deploying an implantable prosthesis valve device at the natural aortic valve position at the entrance to the left ventricle of a myocardium of a patient, the method comprising the steps of:

(a) providing a balloon catheter having a proximal end and a distal end, having a first and second independently inflatable portions, the first inflatable portion located at the distal end of the catheter and the second inflatable portion adjacently behind the first inflatable portion;

(b) providing a guiding tool for guiding the balloon catheter in the vasculature of the patient;

(c) providing a deployable implantable valve prosthesis device adapted to be mounted on the second inflatable portion of the balloon catheter;

(d) guiding the balloon catheter through the patient's aorta using the guiding tool, the valve device mounted over the second inflatable portion of the balloon catheter until the first inflatable portion of the balloon catheter is inserted into the left ventricle, whereas the second inflatable portion of the balloon catheter is positioned at the natural aortic valve position;

(e) inflating the first inflatable portion of the balloon catheter so as to substantially block blood flow through the natural aortic valve and anchor the distal end of the balloon catheter in position;

(f) inflating the second inflatable portion of the balloon catheter so as to deploy the implantable prosthesis valve device in position at the natural aortic valve position;

(g) deflating the first and second inflatable portions of the balloon catheter; and (h) retracting the balloon catheter and removing it from the patient's body.

Furthermore, in accordance with another preferred embodiment of the present invention, the guiding tool comprises a guide wire.

Finally, in accordance with another preferred embodiment of the present invention, there is provided a method for deploying an implantable prosthesis valve device at the natural aortic valve position at the entrance to the left ventricle of a myocardium of a patient, the method comprising the steps of:

(a) providing a balloon catheter having a proximal end and a distal end, having a first and second independently inflatable portions, the first inflatable portion located at the distal end of the catheter and the second inflatable portion adjacently behind the first inflatable portion;

(b) providing a guiding tool for guiding the balloon catheter in the vasculature of the patient;

(c) providing a deployable implantable valve prosthesis device adapted to be mounted on the first inflatable portion of the balloon catheter, and a deployable annular stent device adapted to be mounted over the second inflatable portion of the balloon catheter, the deployable implantable valve prosthesis device and the deployable annular stent kept at a predetermined distant apart;

(d) guiding the balloon catheter through the patient's aorta using the guiding tool, the valve device mounted over the first inflatable portion of the balloon catheter and the deployable annular stent mounted over the second inflatable portion of the balloon catheter, until the first inflatable portion of the balloon catheter is positioned at the natural aortic valve position;

(e) inflating the second inflatable portion of the balloon catheter so that the deployable stent device is deployed within the aorta thus anchoring the deployable annular stent and the coupled valve device in position;

(f) inflating the first inflatable portion of the balloon catheter so as to deploy the implantable prosthesis valve device in position at the natural aortic valve position;

(g) deflating the first and second inflatable portions of the balloon catheter; and (h) retracting the balloon catheter and removing it from the patient's body.

BRIEF DESCRIPTION OF THE FIGURES

To better understand the present invention and appreciate its practical applications, the following Figures are provided and referenced hereafter. It should be noted that the Figures are given as examples only and in no way limit the scope of the invention as defined in the appended claims.

FIG. 3 illustrates an implantable valve according to the present invention mounted over a stent with an inflatable balloon, in a crimped position;

FIG. 4 depicts implantable valve deployment in a natural aortic valve position in accordance with the present invention;

FIGS. 15a to 15c demonstrate a valve with radio-opaque coating, according to the present invention, which allows imaging of the valve motion under angiogram;

DETAILED DESCRIPTION OF THE INVENTION

Figure 1:
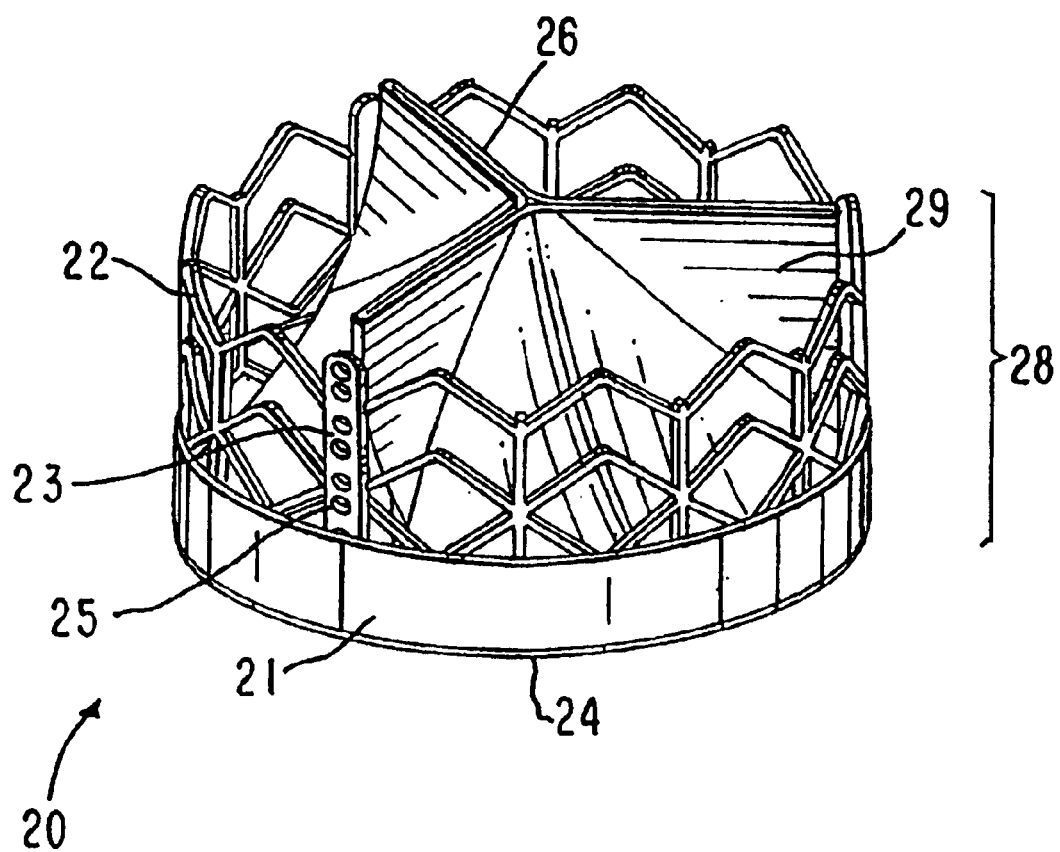
FIG. 1 illustrates an implantable prosthetic tricuspid valve in accordance with a preferred embodiment of the present invention, suitable for percutaneous deployment using a stent or similar deploying means, in its deployed-inflated position.

A main aspect of the present invention is the introduction of several novel designs for an implantable prosthesis valve. Another aspect of the present invention is the disclosure of several manufacture methods for the manufacturing of implantable prosthesis valves in accordance with the present invention. A further aspect of the present invention is the provision of novel deployment and positioning techniques suitable for the valve of the present invention.

Basically the implantable prosthetic valve of the present invention comprises a leafed-valve assembly, preferably tricuspid but not limited to tricuspid valves only, consisting of a conduit having an inlet end and an outlet, made of pliant material arranged so as to present collapsible walls at the outlet. The valve assembly is mounted on a support structure such as a stent adapted to be positioned at a target location within the body duct and deploy the valve assembly by the use of deploying means, such as a balloon catheter or similar devices. In embodiments suitable for safe and convenient percutaneous positioning and deployment the annular frame is able to be posed in two positions, a crimped position where the conduit passage cross-section presented is small so as to permit advancing the device towards its target location, and a deployed position where the frame is radial extended by forces exerted from within (by deploying means) so as to provide support against the body duct wall, secure the valve in position and open itself so as to allow flow through the conduit.

The valve assembly can be made from biological matter, such as a natural tissue, pericardial tissue or other biological tissue. Alternatively, the valve assembly may be made form biocompatible polymers or similar materials. Homograph biological valves need occasional replacement (usually within 5 to 14 years) and this is a consideration the surgeon must take into account, when selecting the proper valve implant according to the patient type. Metal mechanical valves, which have better durability qualities, carry the associated risk of long-term anticoagulation treatment.

The frame can be made from shape memory alloys such as nickel titanium (nickel titanium shape memory alloys, or NiTi, as marketed, for example, under the brand name Nitinol), or other biocompatible metals. The percutaneously implantable embodiment of the implantable valve of the present invention has to be suitable for crimping into a narrow configuration for positioning and expandable to a wider, deployed configuration so as to anchor in position in the desired target location.

The support stent is preferably annular, but may be provided in other shapes too, depending on the cross-section shape of the desired target location passage.

Manufacturing of the implantable prosthetic valve of the present invention can be done in various methods, for example, by dipping, injection, electrospinning, rotation, ironing, or pressing.

The attachment of the valve assembly to the support stent can be accomplished in several ways, such as by sewing it to several anchoring points on the support stent, or riveting it, pinning it, or adhering it, to provide a valve assembly that is cast or molded over the support stent, or use any other suitable way of attachment.

To prevent leakage from the inlet it is optionally possible to roll up some slack wall of the inlet over the edge of the frame so as to present rolled-up sleeve-like portion at the inlet.

Furthermore, floating supports may be added to enhance the stability of the device and prevent it from turning inside out.

An important aspect of certain embodiments of the present invention is the provision of rigid support beams incorporated with the support stent that retains its longitudinal dimension while the entire support stent may be longitudinally or laterally extended.

The aforementioned embodiments as well as other embodiments, manufacturing methods, different designs and different types of devices are discussed and explained below with reference to the accompanying drawings. Note that the drawings are only given for the purpose of understanding the present invention and presenting some preferred embodiments of the present invention, but this does in no way limit the scope of the present invention as defined in the appended claims.

Reference is now made to FIG. 1, which illustrates a general tricuspid implantable prosthesis valve 20 in accordance with a preferred embodiment of the present invention, suitable for percutaneous deployment using an expandable stent or similar deploying means, shown in its deployed position. A valve assembly 28 comprises a conduit having an inlet 24 and an outlet 26, the outlet walls consisting of collapsible pliant material 29 that is arranged to collapse in a tricuspid arrangement. The valve assembly 28 is attached to an annular support stent 22, the one in this figure being a net-like frame designed to be adapted to crimp evenly so as to present a narrow configuration and be radially deployable so as to extend to occupy the passage at the target location for implantation in a body duct. Support beams 23 are provided on annular support stent 22 to provide anchorage to valve assembly 28. Support beams 23 are optionally provided with bores 25 to allow stitching of valve assembly 28 to support beams 23 by thread, wires, or other attachment means.

In the embodiment shown in FIG. 1, a cuff portion 21 of the valve assembly 28 is wrapped around support stent 22 at inlet 24 to enhance the stability. Preferably cuff portion 21 of valve assembly 28 is attached to support beams 23.

Note that the entire valve structure is adapted to be radially crimped and radially expanded, and this lends to provide ease of navigation through narrow passages in the vasculature during positioning of the device and adequate deployment on the final location. This is made possible by the provision of a collapsible support stent structure. However, the support beams remain at all times constant at their length and thus are suitable for serving as the pliable valve assembly's anchorage. The valve assembly is attached to the support stent at the support beams, and due to their constant length there is no need for slack material as the attachment points (25) remain at constant distances regardless of the position of the valve device (crimped or deployed). This is an important feature for this means that the manufacturer of the valve device can make sure the valve assembly is secured and fastened to the support stent at all times. In prior art implantable valve devices the entire support structure changes its dimensions from its initial first crimped position and final deployed position, and this means that in the attachment of the valve assembly to the support structure one must take into consideration these dimension changes and leave slack material so that upon deployment of the device the valve assembly does not tear or deform. In the valve device of the present invention there is no relative movement between the valve assembly and the support beams (along the longitudinal central axis of the device). As a result, the valve device of the present invention acquires greater durability and is capable of withstanding the harsh conditions prevailing within the vasculature and especially the millions of cycles of stress applied by the blood pressure.

The fixed attachment of the valve assembly to the support stent in the valve device of the present invention results in greater stability, enhanced safety, better sealing and consequently longer lifespan. The novel design of the valve device of the present invention leads to longitudinal strength and rigidity whereas its collapsible support structure results in radial flexibility.

Figure 2:
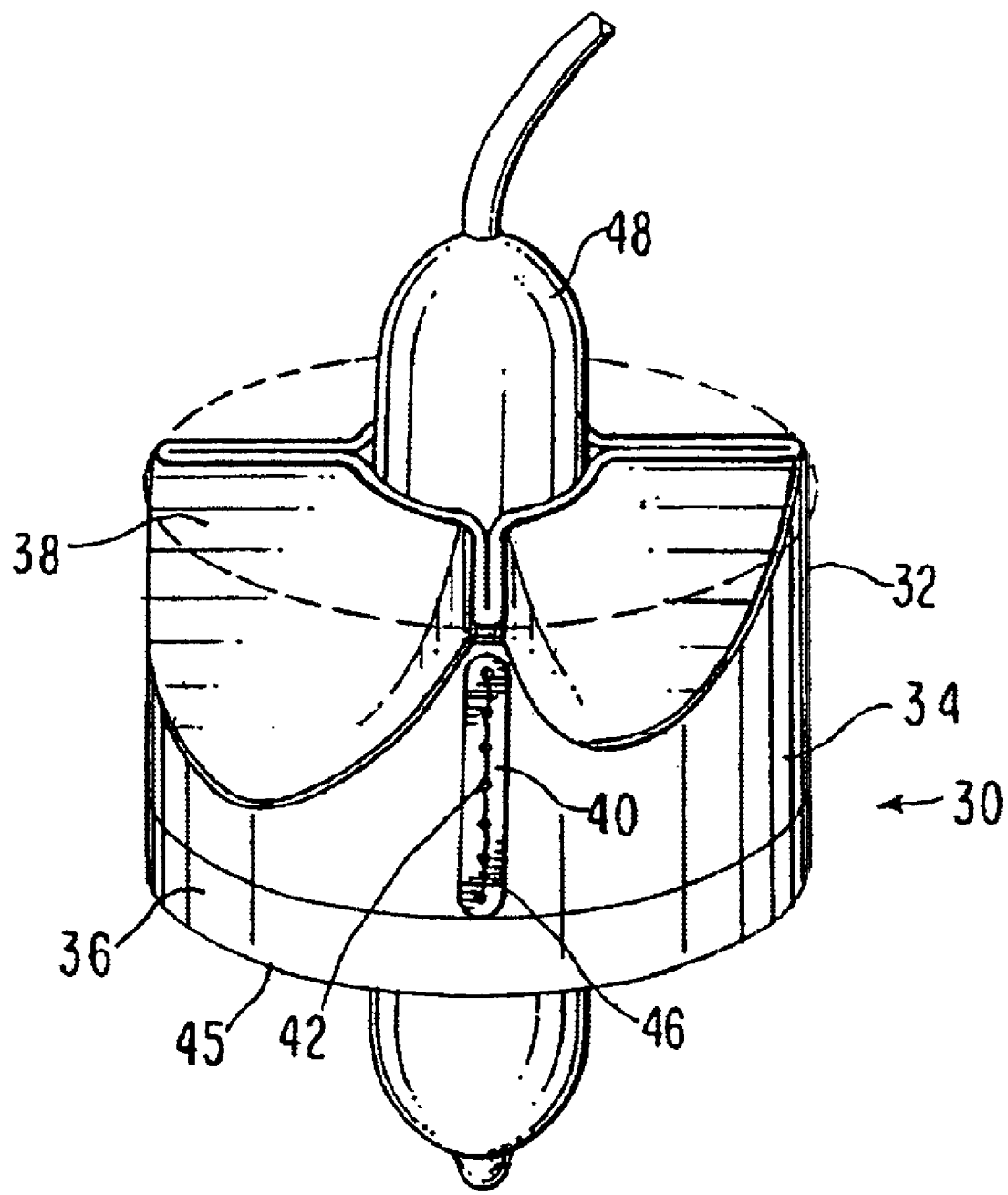
FIG. 2 depicts an implantable valve according to the present invention mounted over a deploying stent with an inflatable balloon.

FIG. 2 depicts an implantable valve 30 mounted on a deployable stent 32. The valve assembly 34 is attached to the deployable support stent 32 (dotted lines) along three substantially equidistant and substantially parallel support beams 40 of constant length, which are part of stent 32. The attachment of valve assembly 34 to stent 32 is facilitated by the support beams 40 to which valve assembly 34 is stitched with thread or fiber 46 (through bores 42 of support beams 40). Outlet leafs 38, which are a slack portion of the valve assembly, dangle inwardly, and the whole device is carried by an inflatable balloon 48, which serves as the deploying device. A portion of the valve assembly 34 at an inlet zone 45 is optionally rolled over support stent 32 at the inlet, making up a rolled sleeve, which enhances the sealing of the device at the valve inlet.

FIG. 3 demonstrates an implantable valve mounted to a stent 50 with an inflatable balloon 52, in a crimped position. The support stent 50 is initially crimped about the balloon 52 so that is presents a narrow cross-section and is thus suitable for percutaneous catheterization and deployment.

FIG. 4 depicts an implantable valve deployment in a natural aortic valve position. The implantable valve is advanced while mounted over the balloon 52 until it reaches the desired target location 54 in a body duct, for example, aorta 56. The balloon is inflated and the support stent 50 expands radially to take up its position.

Figure 5:
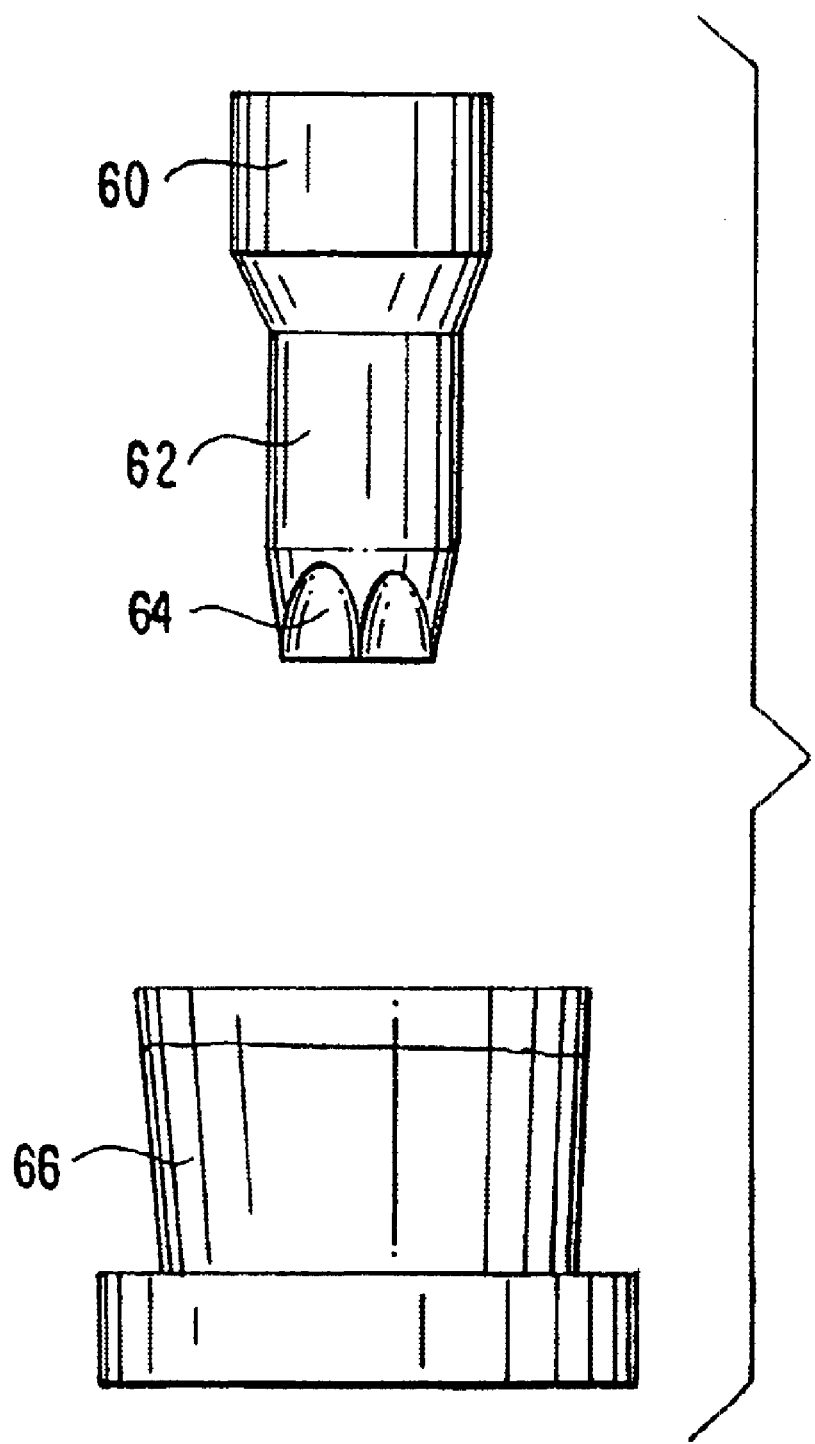
FIG. 5 demonstrates manufacturing a polyurethane implantable valve in a dipping technique according with the present invention.

FIG. 5 demonstrates the manufacture of a polyurethane valve in a dipping technique. A dipping mandrel 60 is provided with a tubular portion 62 with surfaces 64 that correspond to the collapsible valve leaflets to be manufactured. Mandrel 60 is dipped into a dissolved polyurethane bath 66 and is coated with a polyurethane coating in the desired form of the valve. Then, after the polyurethane coating has hardened sufficiently, the completed valve is removed from mandrel 60.

Figure 6A:
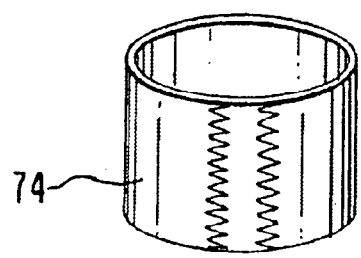
FIGS. 6a to 6e illustrate manufacturing of an implantable valve by forging according to the present invention.
Figure 6B:
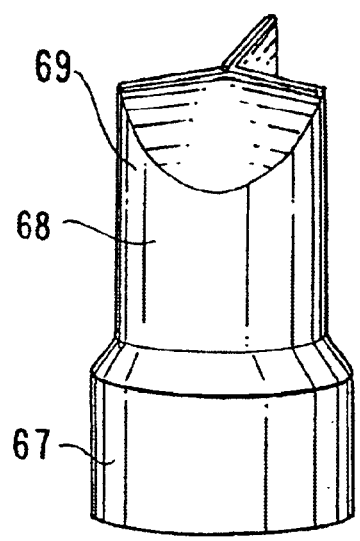
Figure 6C:
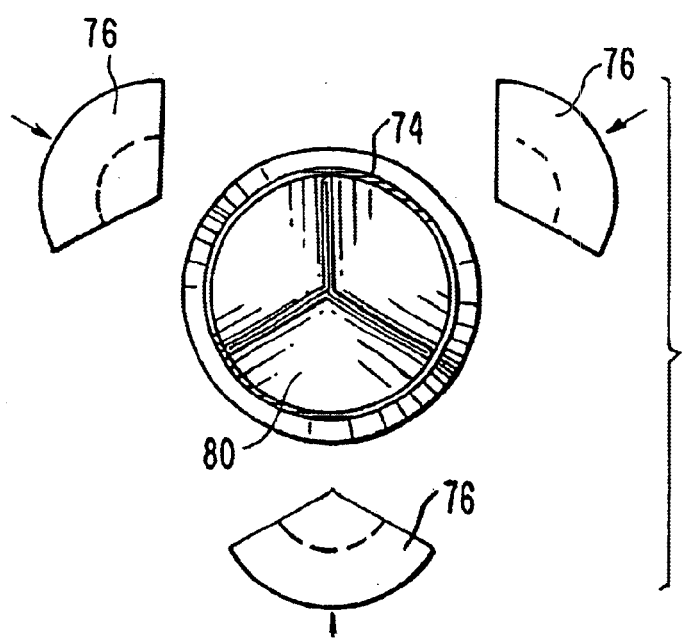
Figure 6D:
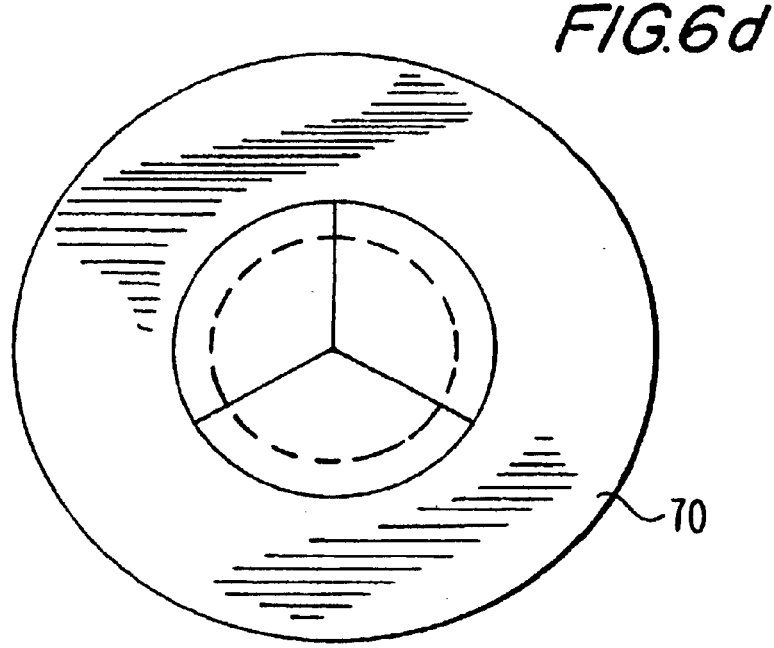
Figure 6E:
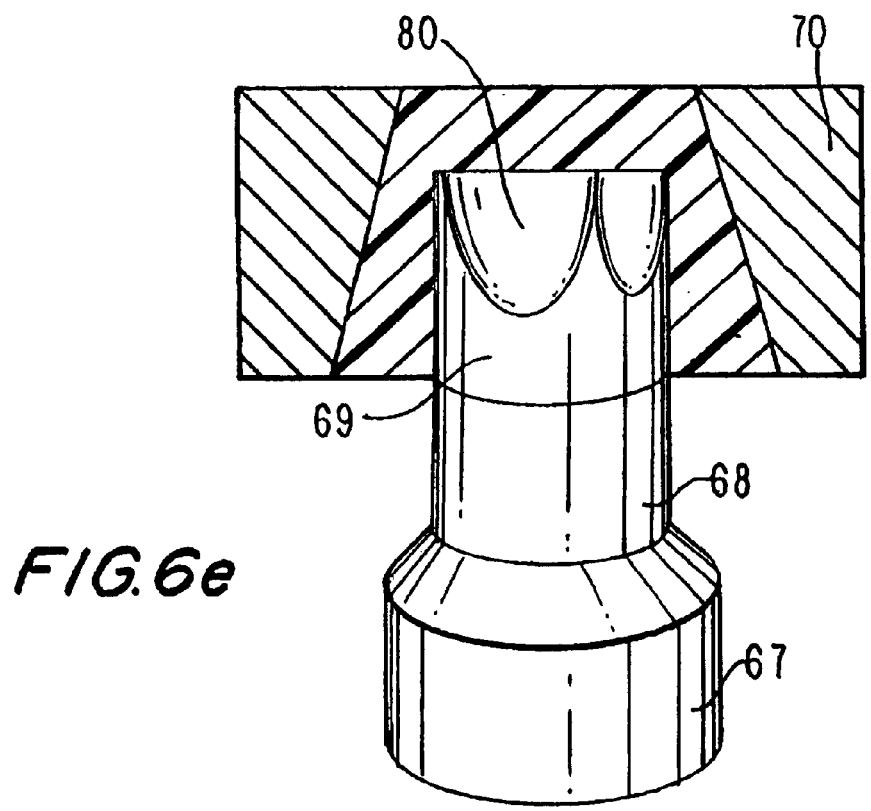

FIGS. 6a to 6e illustrate manufacturing an implantable valve by forging. A suitable tubularly shaped material 74 is placed tightly on a tubular portion 68 of mandrel 67, covering the cusp portion 69. Flexible inserts 76 are pressed to mandrel 67, forging the tubular material to mandrel shape 80. A tapered ring 70 holds the flexible inserts in place as the whole mold is placed in a hot oven regulated to a desired temperature, which is lower than the material's melting point. FIG. 6e illustrates a sectional side view of the mandrel and a cross cut portion of the mold. The mold is made to press inwardly on the mandrel, which is covered with the valve material. As a result the material takes up the desired shape. The materials used can vary, for example, polyurethane (PU), polyethylene terphthalate (PET), or any other suitable material, which may be formed by heating.

Figure 7A:
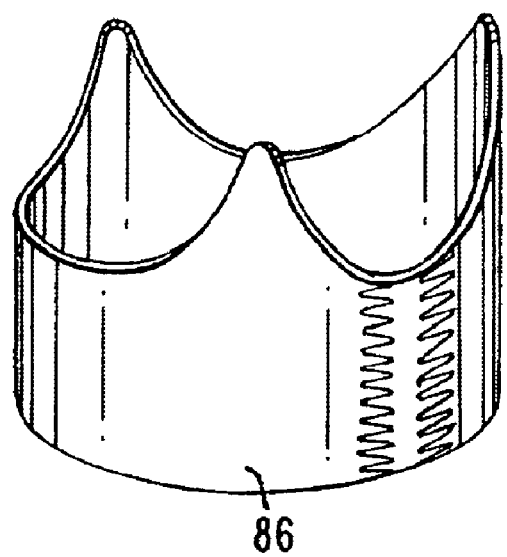
FIGS. 7a and 7b demonstrate composite valve, which has polyurethane (PU) leaflets and Polyethylene terphthalate (PET) tubular-crown shaped construction, according to the present invention.
Figure 7B:
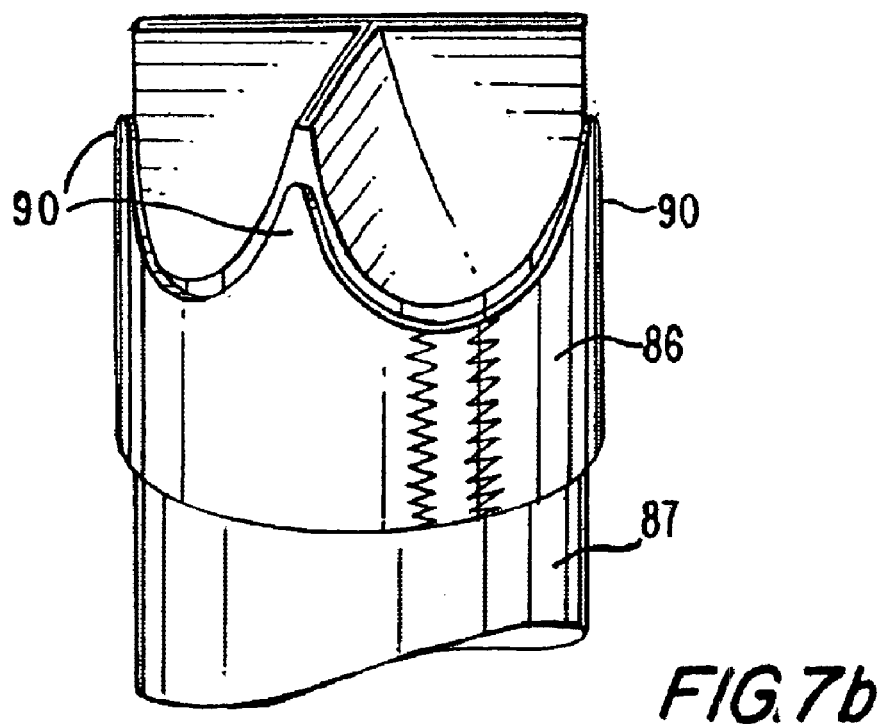

FIGS. 7a and 7b demonstrate a method of manufacturing a composite valve, which has PU leaflets and PET tubular construction with a crown shape. PU is an excellent fatigue resistant material but is sensitive to tear. The PU is reinforced by the PET crown to allow safe attachment to a stent by means of stitching, riveting, or any other suitable attachment method. A PET crown 86 is placed on a mandrel 87, which is then (turned and) dipped in a container of dissolved PU. The manufactured device is a valve assembly having leaflets 88 composed of pure PU, and thus fatigue resistant, and a main body made of PET with protruding attachment portions 90 suitable for attachment built in the PU.

Figure 8A:
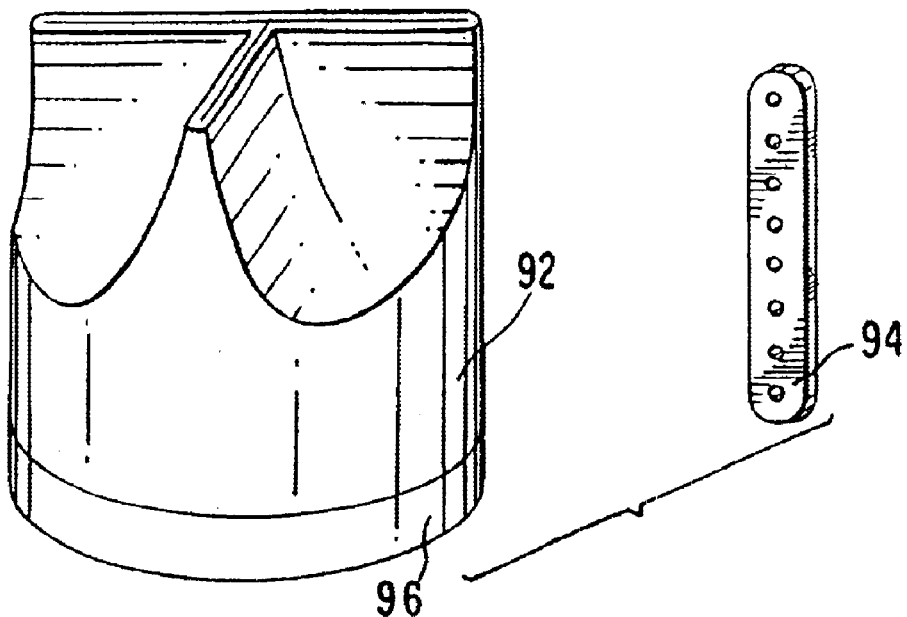
FIGS. 8a and 8b depict a manufacture process of a composite valve made of flexible PU leaflets, rigid PU construction for mounting and a PET tubular end.
Figure 8B:
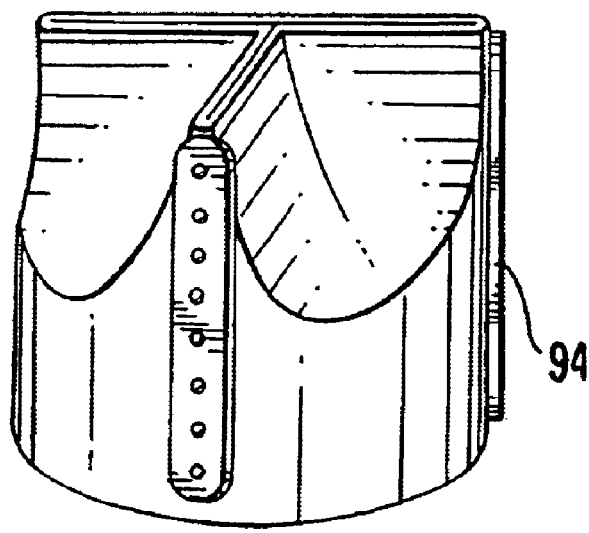

FIGS. 8a and 8b demonstrate a method of manufacturing a composite valve, which is based on flexible PU 92 for as the main body of the valve, rigid PU support beams 94 serving for the attachment area, and PET sleeve 96 portions for the valve inlet. The need for a rigid portion for attachment (support beams 94) is explained by the tendency of the flexible, fatigue resistant material to tear as already explained. The advantage of the stiff PU support beams is that they are chemically adhered to the main body, and this improves the overall durability of the valve due to reduction of inner forces and friction in the attachment area specially attachment between two different materials. The valve is dipped in the method mentioned with reference to FIG. 5, and the rigid PU support beam 94 is created by way of mold injection, machining or any other suitable way. The rigid PU support beam 94 is placed on the valve and then dipped into the container of dissolved PU. This is done while the valve is positioned on the mandrel (not shown). This method provides the ability to composite several materials into one body and, by that, gain the advantage of the various properties of the materials as they are needed in different areas of the prosthesis.

Figure 9:
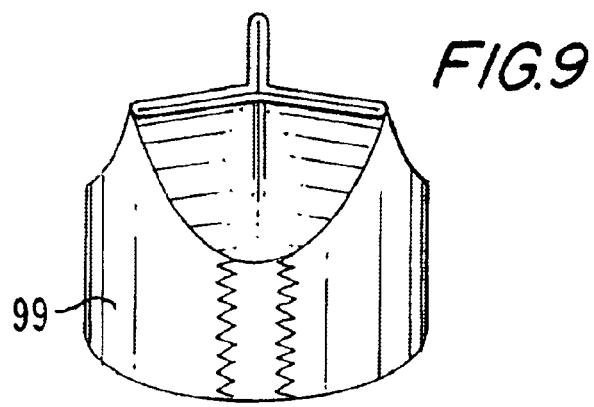
FIGS. 9 to 9i demonstrate different methods of attachment between the valve and stent according to the present invention.
Figure 9A:
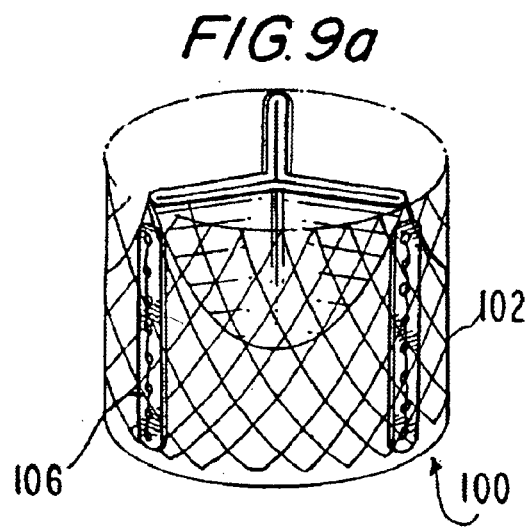
Figure 9B:
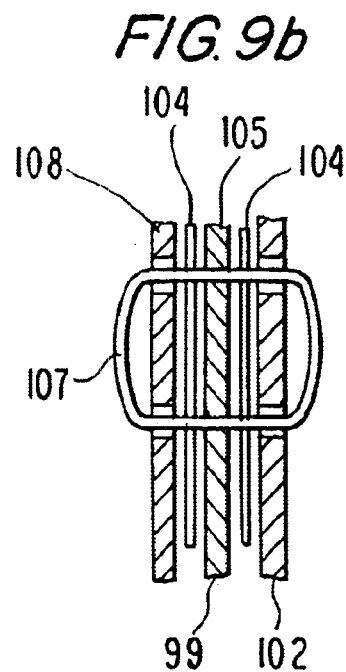
Figure 9D:
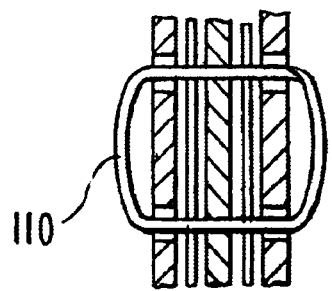
Figure 9C:
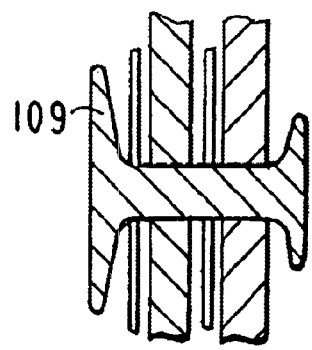
Figure 9E:
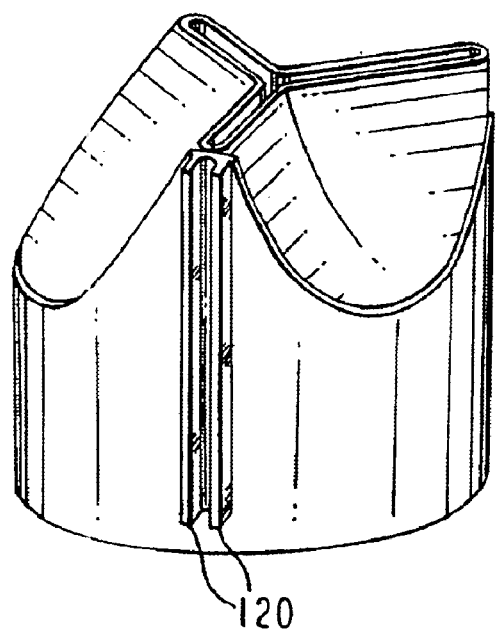
Figure 9F:
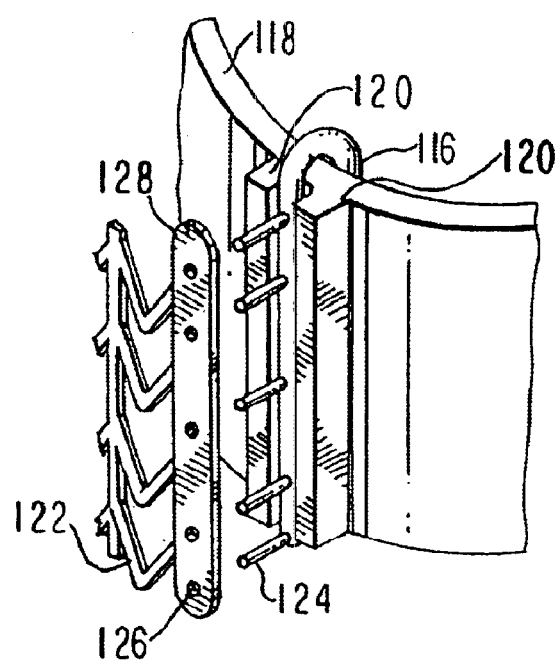
Figure 9G:
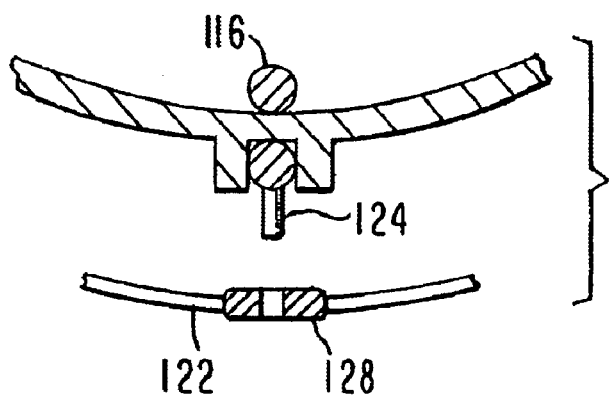
Figure 9H:
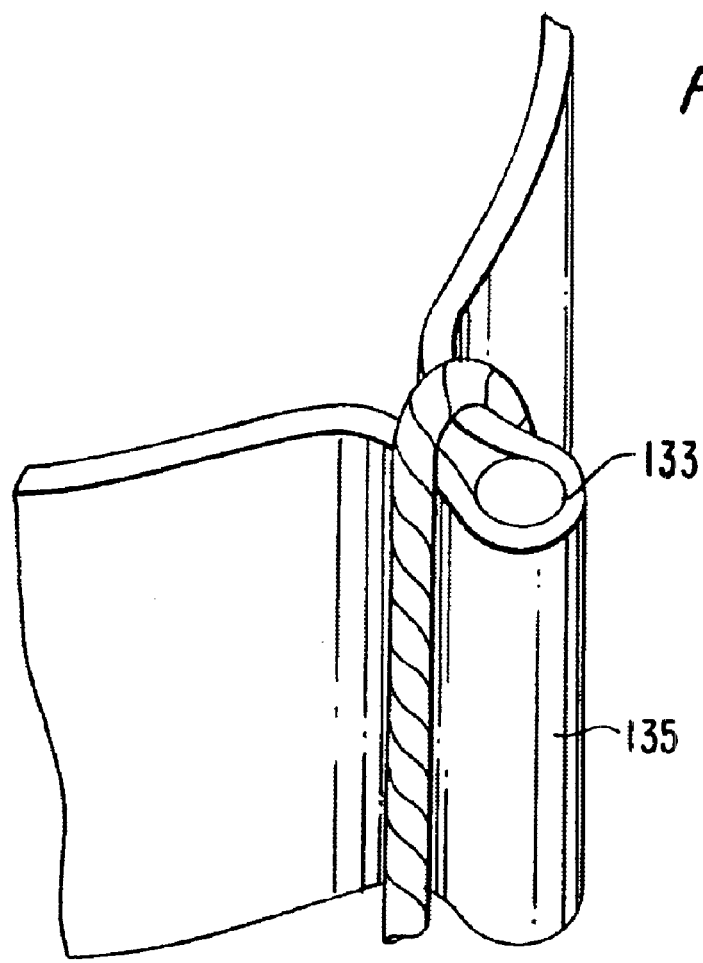
Figure 9I:
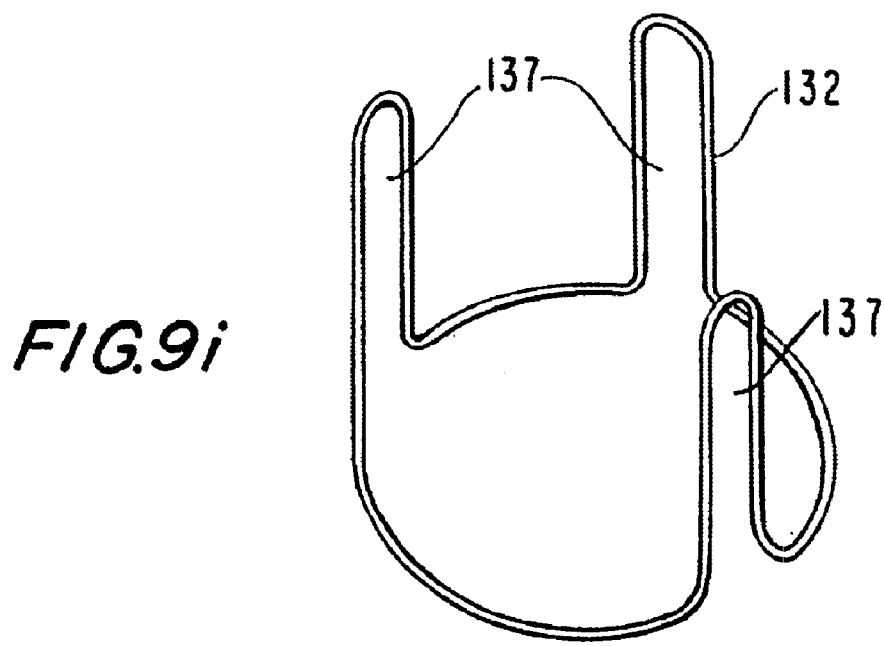

FIGS. 9 to 9i demonstrate different methods of attachment between a valve assembly and the support stents. A valve assembly 99 shown in FIG. 9 is incorporated into valve 100 shown in FIG. 9a, where a support stent 102 is attached to valve assembly 99 through support beam 106. A detail is shown in FIG. 9b, where, in cross-section, it can be seen that layer 108 is an optional inner support made of stainless steel or rigid polymeric material, valve assembly 99 comprises a PET layer 105 coated with a PU layer 104, with the outer support beam 106. Connector 107 is a connecting wire made of a strong material, such as stainless steel. FIG. 9c illustrates an alternative arrangement for attachment by a rivet 109, and in FIG. 9d the attachment is achieved by a suture 110.

FIGS. 9e to 9g show an attachment method comprising shaped rigid members 116, preferably made from metal, which tightly hold the PU valve material 118 by fitting in between a PU U-shaped nest 120 and are attached to a stent 122 by extruding portions 124 that are provided on U-shaped rigid member 116, which fit the bores 126 of the support beam 128 of the stent 122. FIGS. 9h and 9i show another attachment method, where rigid support beams in the form of frame construction 132 are provided, and the valve assembly pliant material 135 made of a tubular material is inserted through a gap 137 in the frame. After insertion, a fastening rod 133 is inserted through the pocket formed between the pliant material and the frame and holds the valve in position.

Figure 10:
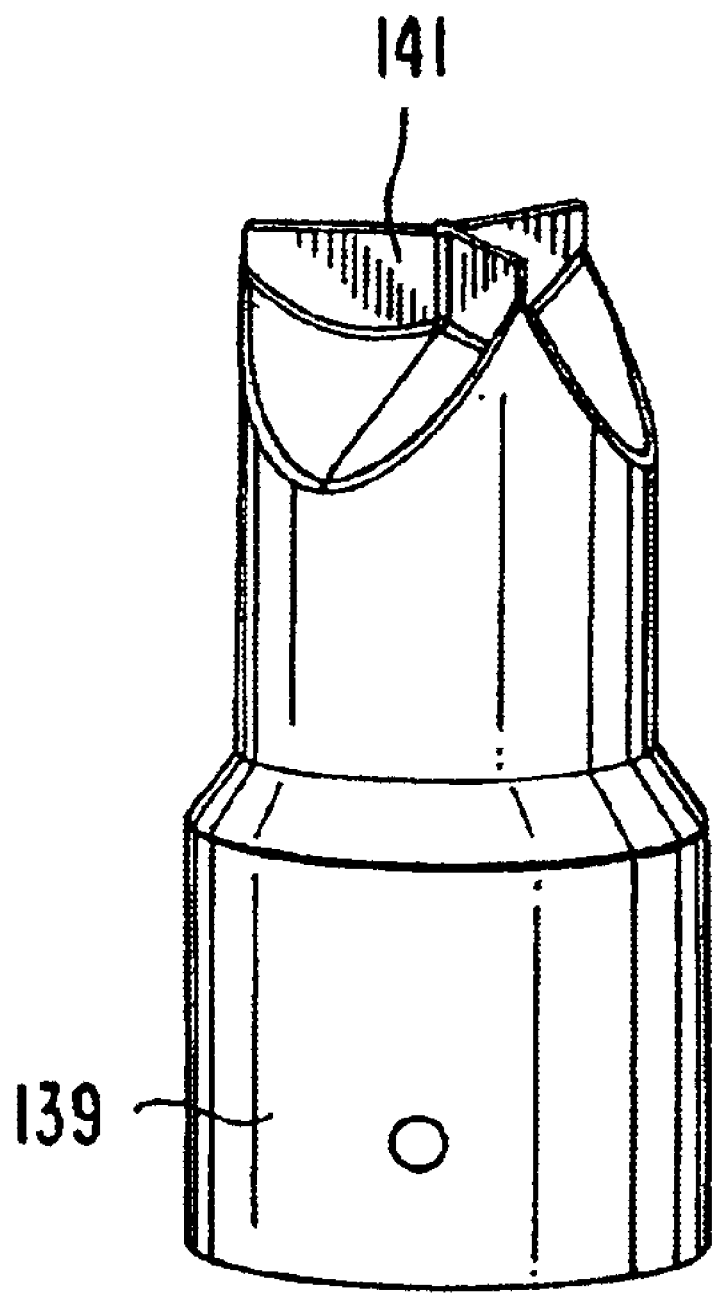
FIG. 10 illustrates a dipping mandrel with an extra portion, which improves the sealing ability of the valve, according to the present invention.

FIG. 10 illustrates a dipping mandrel 139 with an extending portion 141, which improves the sealing ability of the valve. Since the valve is attached to a collapsible stent and is itself collapsible, it is difficult to determine the exact shape of the valve after crimping and deploying. It is of major importance that sealing will be achieved. By adding the extension 141 the leaflets are made longer than needed to exactly close the outlet, and therefore when they are in the collapsed state, substantial portions of the leaflets fall on each other creating better sealing.

Figure 11A:
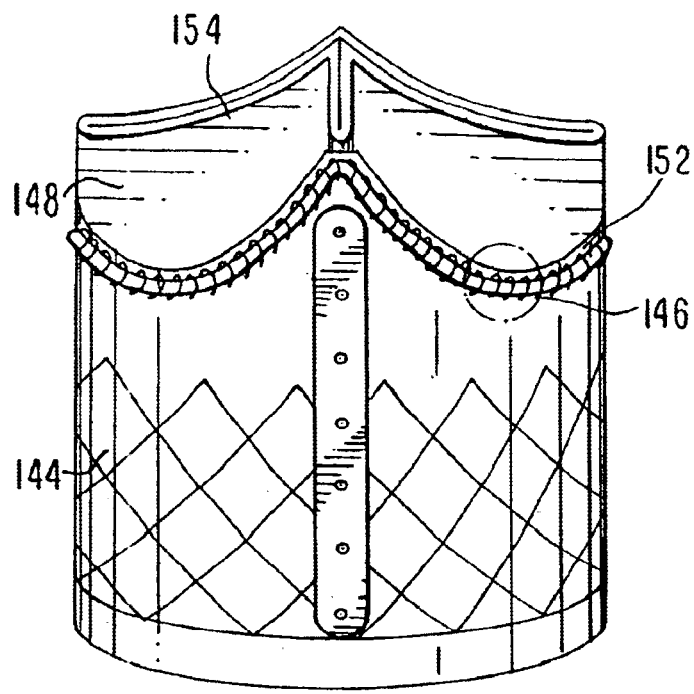
FIGS. 11a to 11c illustrate a valve mounted on a stent with an extra support, which improves the force distribution on the valve material and facilitates prolonged durability of the valve, according to the present invention.
Figure 11B:
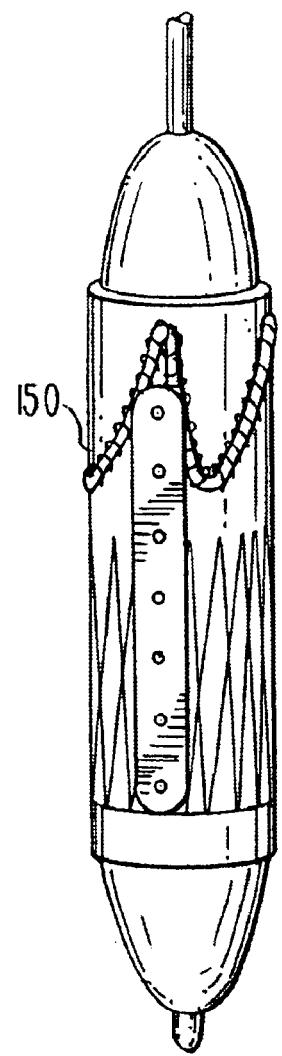
Figure 11C:
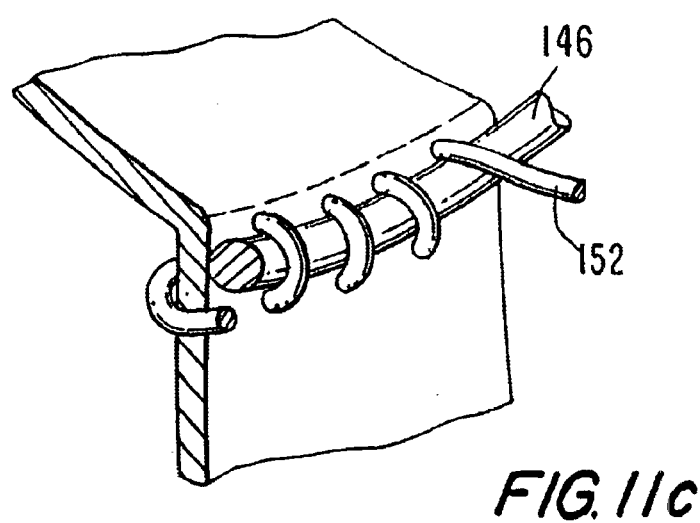

FIGS. 11a to 11c illustrate a valve assembly mounted on a support stent 144 with interlaced strengthening wire 146, which improves the force distribution on the valve material and facilitates prolonged durability of the valve. The support is in the form of a wire, which has a crown shape as the shape of the three cusp valve base 148, it also has the ability to be crimped 150 to a small diameter, together with the stent, valve and balloon, as shown in FIG. 11b. The forces applied to the valve edge 148 while working, are applied to the attachment points, by making the attachment line longer we reduce the force on each attachment point. In this support method the valve is attached by suturing 152 the entire line to the extra support wire 146. This wire can be made of stainless steel, nickel titanium alloy such as nitinol, or polymeric material. The support suture renders the valve assembly default fault lines where the valve material more readily flexes, thus ensuring proper operation of the valve flaps (leaflets). Optionally the valve assembly shown in FIGS. 11a to 11c can be mounted on a support stent such as the one described herein or similar supporting structures. The strengthening wire is interlaced in the valve assembly at the outlet of the conduit so as to define a fault line about which the collapsible slack portion 154 of the valve assembly may flap.

Figure 12A:
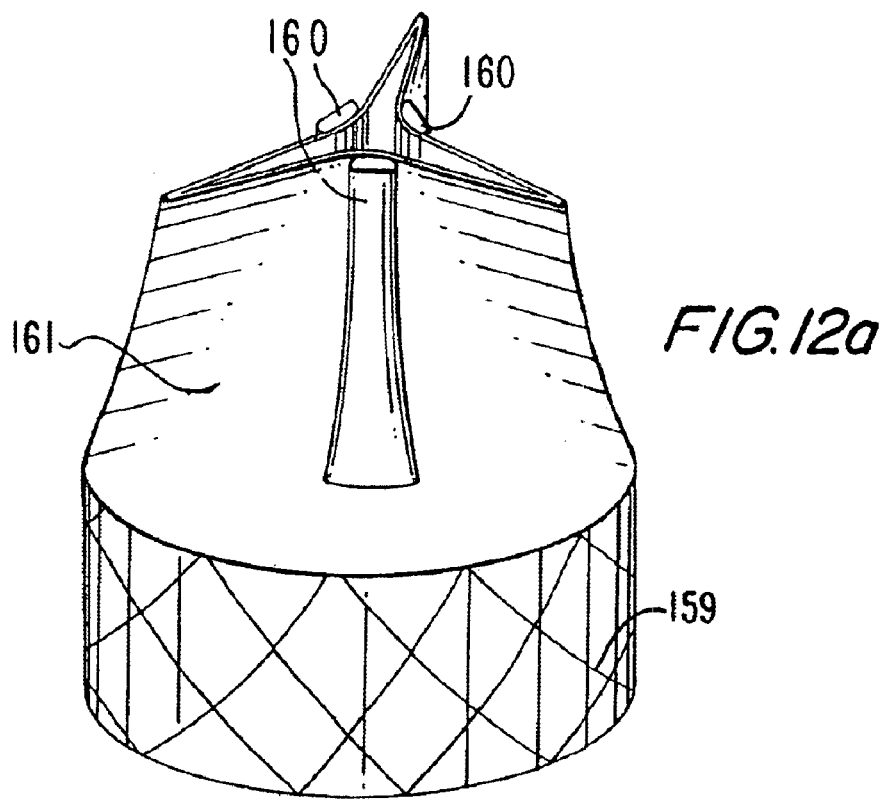
FIGS. 12a to 12c depict a valve with rigid supports according to the present invention, located substantially in the center of its leaflets. This design allows the valve leafs to perform without outer support.
Figure 12B:
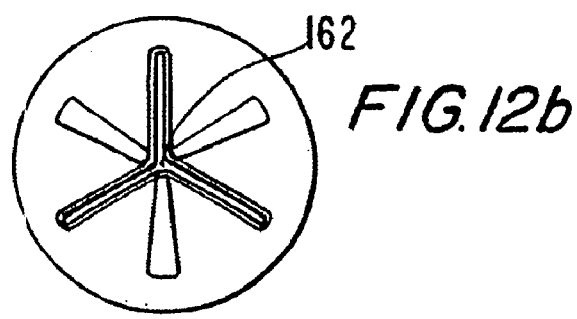
Figure 12C:
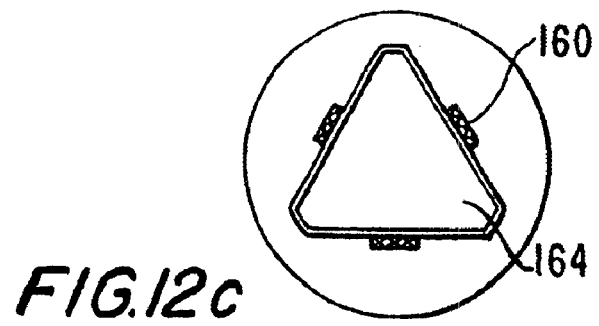

FIGS. 12a to 12c depict a valve device provided with a stent 159 and substantially equidistant rigid support beams 160, interlaced or attached to the slack portion of the valve assembly material 161, arranged longitudinally. This design allows the valve leaflets to perform without outer support. The support in standard valves is by tying the upper edge of the cusp to a rigid embodiment, so that it reacts to the load as a suspension bridge. In this new design the prevention of collapsing is achieved similar to an Indian tent, i.e., the rigid supports lean on each other 162 when the valve is closed but do not interfere in opening 164 when the valve is open.

Figure 13A:
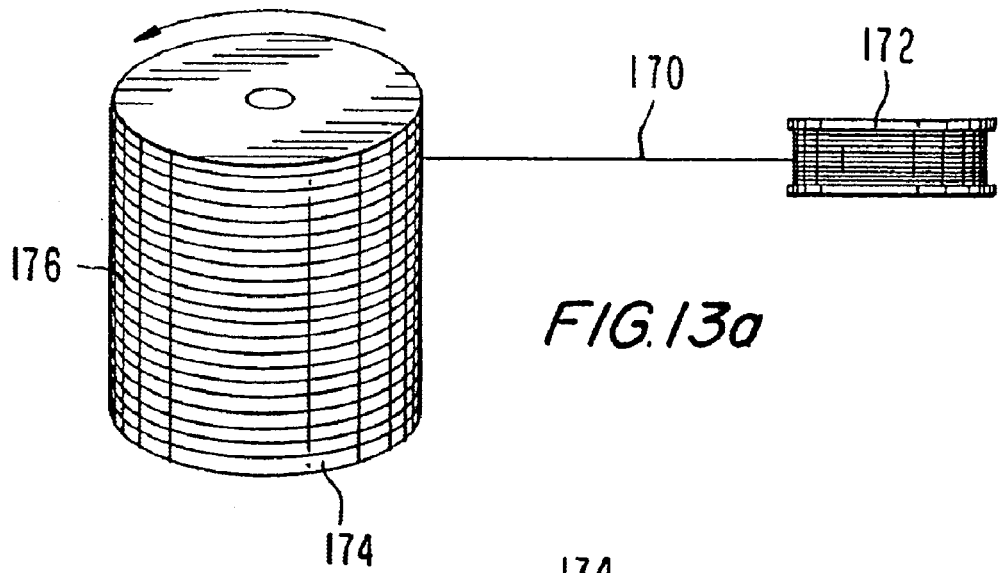
FIGS. 13a to 13c illustrate the manufacturing of a reinforced PU tube composed of strong fiber from PU, PET or other and a softer PU coating, for serving as the supporting structure.
Figure 13B:
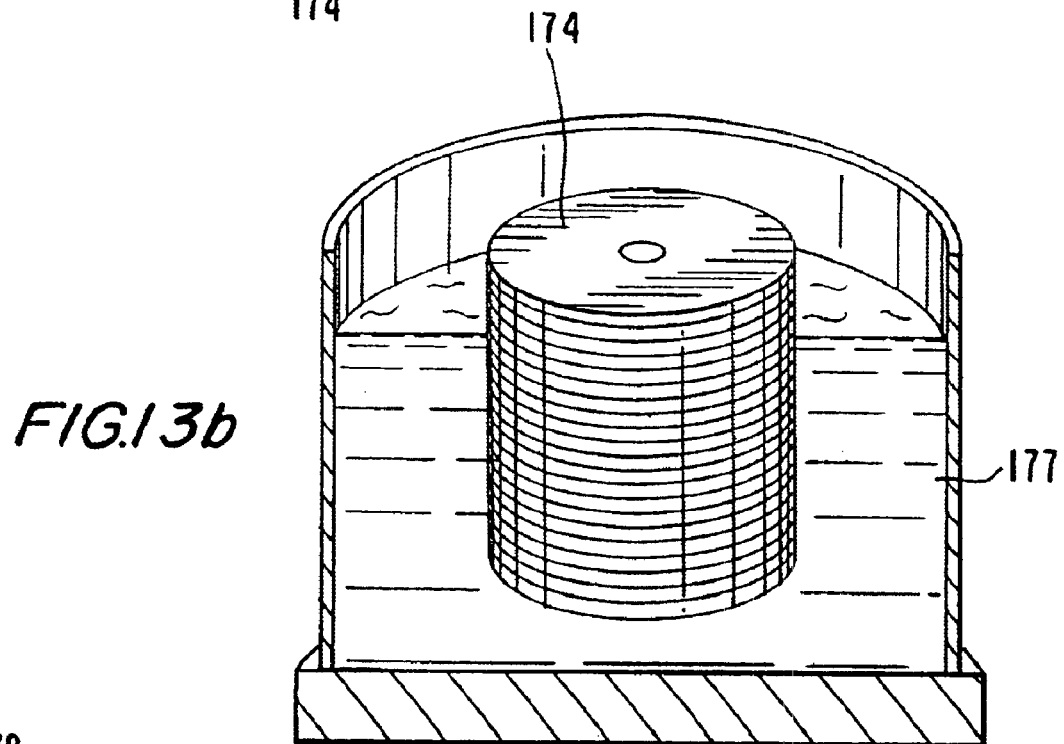
Figure 13C:
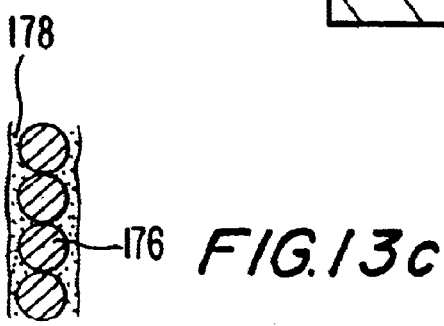

FIGS. 13a to 13c illustrate the manufacturing of a valve assembly in accordance with another preferred embodiment of the present invention. At first a polyurethane thread line 170 is fed from a PU supply 172, and coiled around a cylindrical drum 174 to form coil 176. Then, drum 174 with coil 176 is dipped in a PU bath 177, and a second layer 178 of the PU coats coil 176, making it a stronger construction capable of withstanding tearing forces both laterally and in other directions. Incorporating two different types of materials—such as PU and PET—may render greater durability and endurance to the valve assembly. This material is an alternative material to be used in the forging method shown in FIG. 6.

Figure 14:
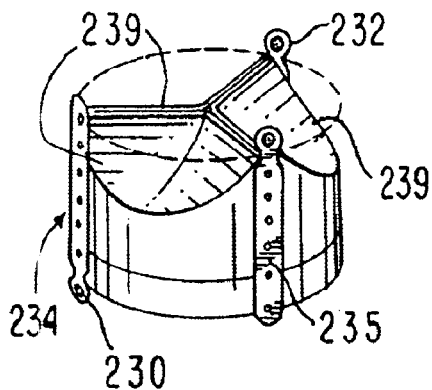
FIGS. 14 to 14c demonstrate incorporation of heavy metal markers on the stent, according to the present invention. These markers allow orientation control while positioning the device at the required location.
Figure 14A:
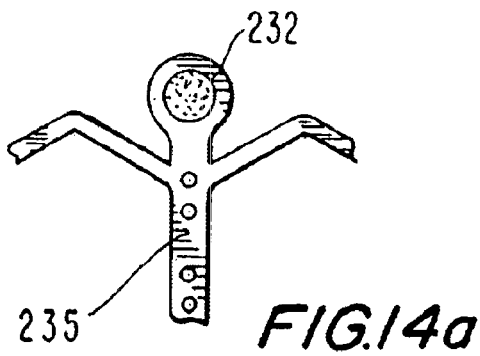
Figure 14B:
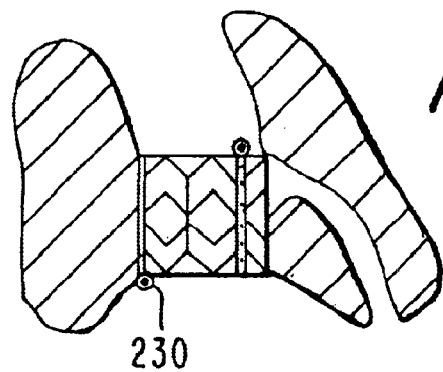
Figure 14C:
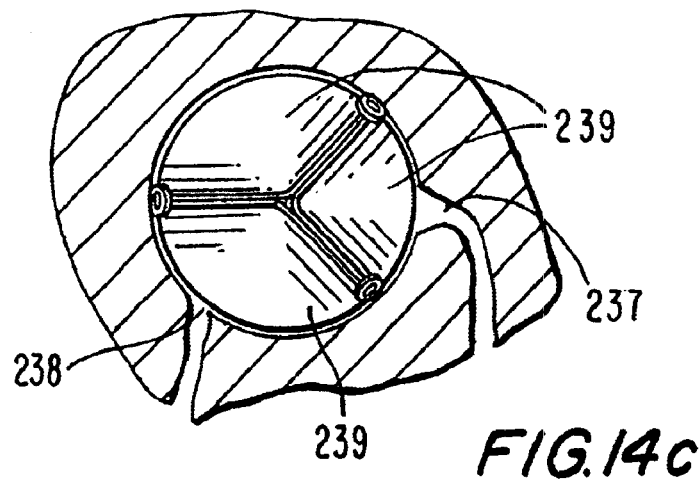

FIGS. 14 to 14c demonstrate the incorporation of heavy metal markers on the stent, which markers allow observation and thereby adjustment of orientation while placing the device in the required location. Heavy metals are radiopaque, that is, they are conspicuous on an angioscopic image, which is a two-dimensional image. Since the coronary arteries ostia 237 and 238 are located near the typical valve deployment location and must stay open, it is extremely important to make sure that the deployed valve assembly is not blocking a coronary ostium. In some cases the stent is lower than the ostium and in those cases it will stay open, but in some cases as shown in these figures it is necessary to make sure that the stent portion 239 that is connecting the valve supports 235 is opposite the coronary ostia, and in that way the blood supply is preserved through the stent struts. Two heavy metal markers 232 are attached at the outlet side, one marker 230 at the inlet side. It is possible to adjust the angiogscopic view to the plane of the left coronary as shown in FIG. 14b and anatomically locate the other accordingly. If the two upper markers 232 are placed in the radiographic two dimensional image, one on top of the other, and the low marker 230 on the opposite side, we make sure that the coronaries are open to blood flow as seen in FIG. 14c. Gold, platinum, iridium or tantalum are all biocompatible materials suitable for the markers described above.

FIGS. 15a to 15c illustrate a valve with a portion of radio-opaque material 267 such as a thread of gold at the sealing edge. When a valve is implanted, it is very important to have clear indications of how the valve is functioning in vivo; pressure measurements, flow visualization, and doppler measurements are utilized. It is also possible to examine the valve by ultrasound methods, however, observing the opening and closing of the valve cusps on a monitor. FIG. 15b is an angiographic image 268 of the open valve, while image 169 in FIG. 15c is the closed position as seen on the angiogram.

Figure 16A:
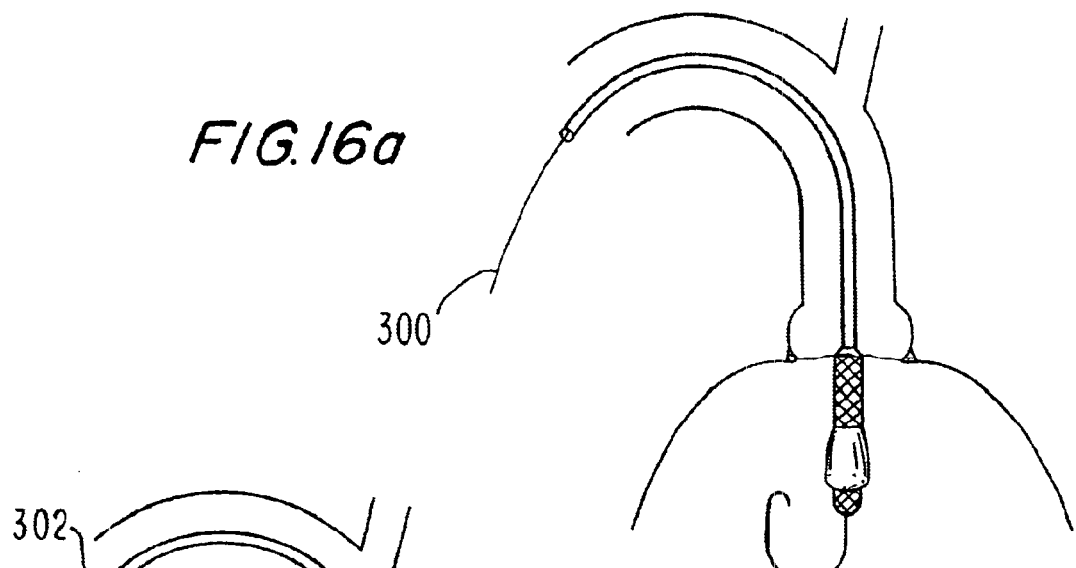
FIGS. 16a to 16c illustrate a procedure, which helps in accurate positioning the valve device with respect to the longitudinal orientation.
Figure 16B:
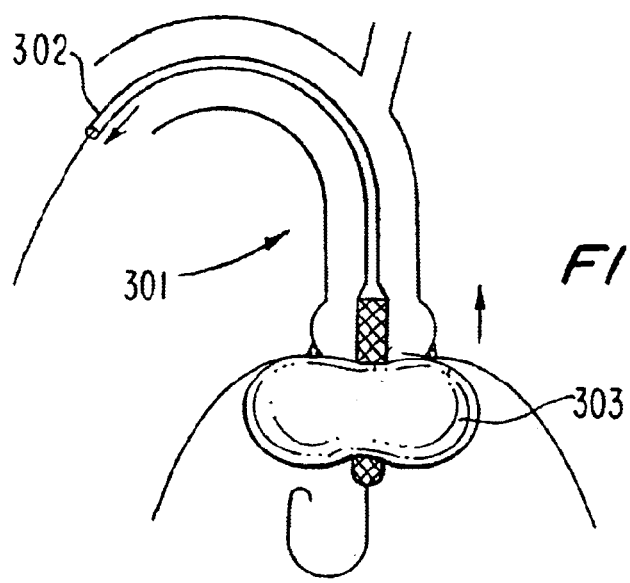
Figure 16C:
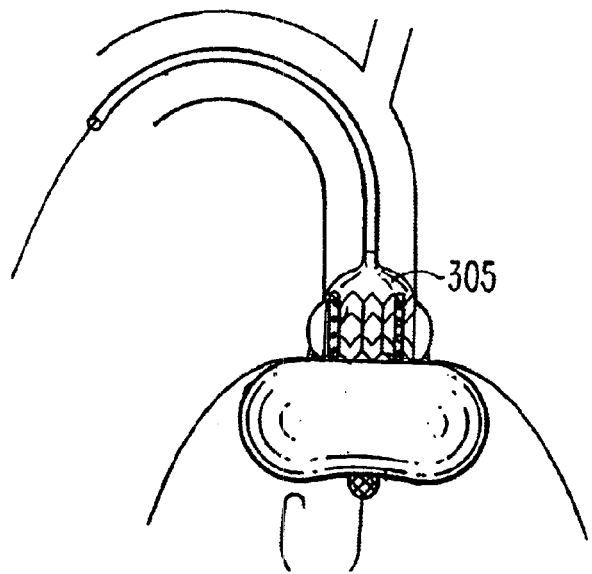

FIGS. 16a to 16c illustrate a procedure, which helps in placing the device in the longitudinal position. It is very important to place the device in the correct longitudinal position, for if it is too deep in the left ventricle it may interfere with the mitral valve function by improper closing or function of the valve. If it is positioned too high it may migrate, it may leak via the sinus cavities, which are located around it, and/or it may block the coronaries. It is a necessary task to position the valve prosthesis in a narrow target location. In FIG. 14 a method of lateral orientation placement is shown, and FIGS. 16a to 16c illustrate a longitudinal positioning. The valve device (the valve assembly and the support stent) is placed on an inflatable balloon catheter, comprising double independently inflatable chambers 303, 305, and is inserted into the left ventricle 302 in the crimped position and guided over a guiding stylet or guide wire 300. The balloon, which is larger than the annulus diameter when inflated, is inflated in the left ventricle 302, and then the whole device is pulled slightly backwards. The balloon is supported on the inner part of the annulus 303, allowing positioning of the device in the exact desired position. In addition, it temporarily blocks the blood flow, and that improves the ability to hold the device in place while inflating it. The next step is inflating the second balloon 305, which deploys the valve device in the desired location.

The method for deploying an implantable prosthesis valve device at the natural aortic valve position at the entrance to the left ventricle of a myocardium of a patient, as depicted in FIGS. 16a, 16b and 16c, comprises the steps of:

(a) providing a balloon catheter having a proximal end and a distal end, having a first and second independently inflatable portions, the first inflatable portion located at the distal end of the catheter and the second inflatable portion adjacently behind the first inflatable portion;

(b) providing a guiding tool for guiding the balloon catheter in the vasculature of the patient;

(c) providing a deployable implantable valve prosthesis device adapted to be mounted on the second inflatable portion of the balloon catheter (d) guiding the balloon catheter through the patient's aorta using the guiding tool, the valve device mounted over the second inflatable portion of the balloon catheter until the first inflatable portion of the balloon catheter is inserted into the left ventricle, whereas the second inflatable portion of the balloon catheter is positioned at the natural aortic valve position;

(e) inflating the first inflatable portion of the balloon catheter so as to substantially block blood flow through the natural aortic valve and anchor the distal end of the balloon catheter in position;

(f) inflating the second inflatable portion of the balloon catheter so as to deploy the implantable prosthesis valve device in position at the natural aortic valve position;

(g) deflating the first and second inflatable portions of the balloon catheter; and (h) retracting the balloon catheter and removing it from the patient's body.

FIG. 17 describes a positioning of a valve device 310 using an additional deployable stent 320. There are several problems that may be encountered while deploying the stent and valve in the aortic valve location: blockage of coronaries may occur that is dangerous if the diameter of the stent is similar to that of the coronaries aortic root 309. Secondly, migration of the whole device may also occur, which is a dangerous possibility, and there is the problematic challenge of exact positioning of the valve device that is very difficult to accomplish, as already explained. The newly special designed device with a double diameter inflatable balloon and double stent design allows placement of the device in a way that coronaries will not be blocked because of a safe difference that is kept between the diameters, longitudinal placing is less sensitive because of the small diameter which ensures prevents over expansion of the valved prosthesis. The distal stent 320, which contains no valve, is expanded into the ascending aorta, while the proximal stent 310 is placed simultaneously in the annular position. This placement method is less challenging due to the smaller diameter of the proximal stent 310 which ensures that the mitral valve is safe too dimensions are preserved, and the additional stent decreases the risk of device migration. It is safer to over dilate in the aorta, which is not true for the annulus.

Figure 17A:
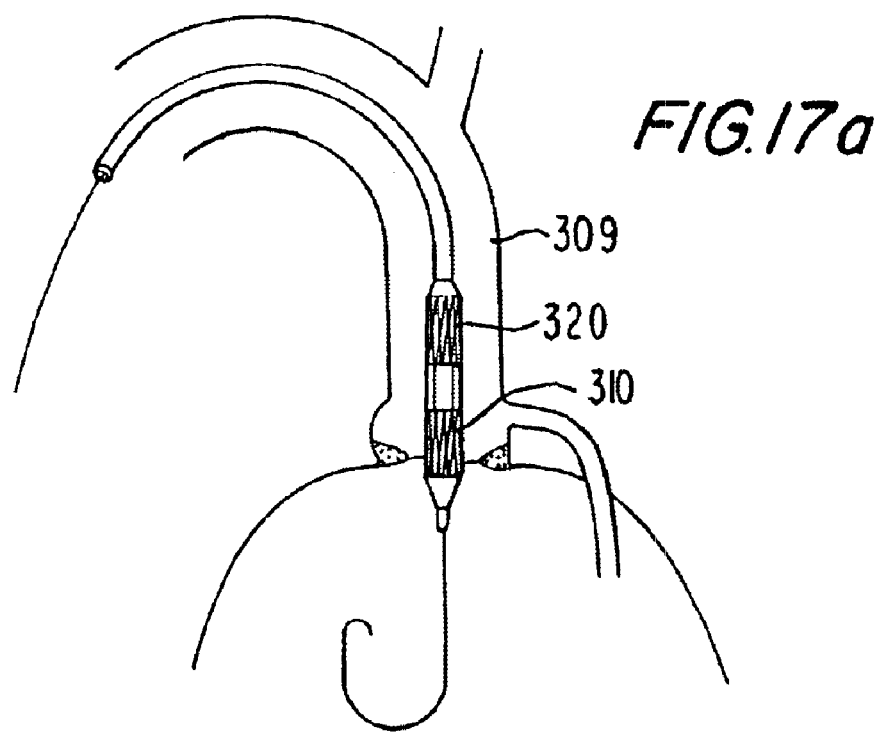
FIGS. 17a and 17b describe a valve device according to the present invention, comprising one valve assembly mounted on a stent and an additional portion with a stent only. This allows placing the device in a way that coronaries are not blocked, longitudinal positioning thus becomes less sensitive and the extra stent decreases the risk of device migration within the vasculature.
Figure 17B:
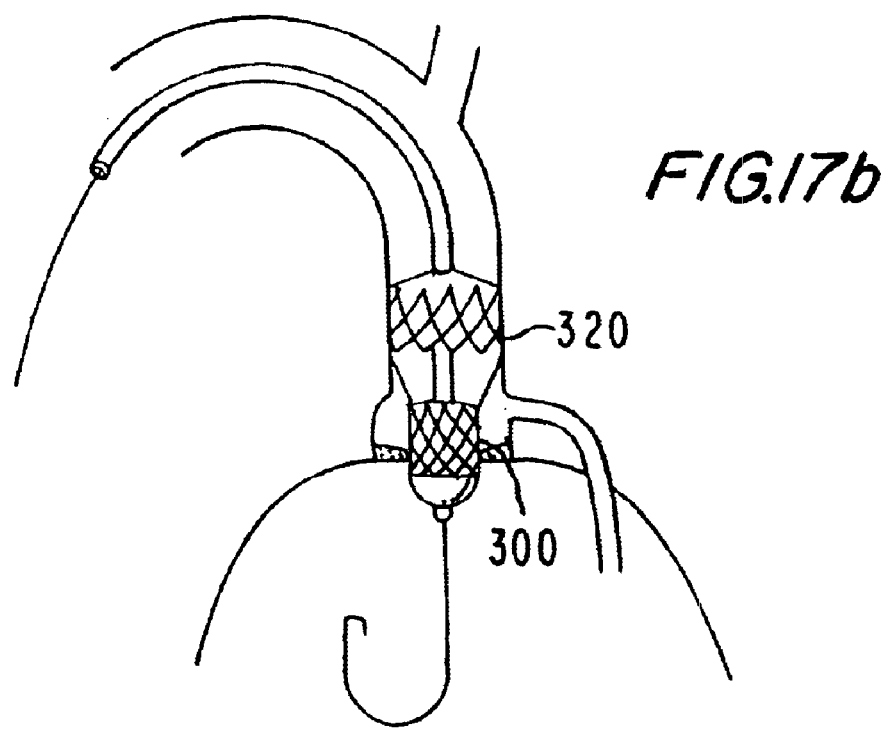

The method for deploying an implantable prosthesis valve device at the natural aortic valve position at the entrance to the left ventricle of a myocardium of a patient, as depicted in FIGS. 17a and 17b, comprises the steps of:

(a) providing a balloon catheter having a proximal end and a distal end, having a first and second independently inflatable portions, the first inflatable portion located at the distal end of the catheter and the second inflatable portion adjacently behind the first inflatable portion;

(b) providing a guiding tool for guiding the balloon catheter in the vasculature of the patient;

(c) providing a deployable implantable valve prosthesis device adapted to be mounted on the first inflatable portion of the balloon catheter, and a deployable annular stent device adapted to be mounted over the second inflatable portion of the balloon catheter, the deployable implantable valve prosthesis device and the deployable annular stent kept at a predetermined distant apart;

(d) guiding the balloon catheter through the patient's aorta using the guiding tool, the valve device mounted over the first inflatable portion of the balloon catheter and the deployable annular stent mounted over the second inflatable portion of the balloon catheter, until the first inflatable portion of the balloon catheter is positioned at the natural aortic valve position;

(e) inflating the second inflatable portion of the balloon catheter so that the deployable stent device is deployed within the aorta thus anchoring the deployable annular stent and the coupled valve device in position;

(f) inflating the first inflatable portion of the balloon catheter so as to deploy the implantable prosthesis valve device in position at the natural aortic valve position;

(g) deflating the first and second inflatable portions of the balloon catheter; and (h) retracting the balloon catheter and removing it from the patient's body.

Figure 18B:
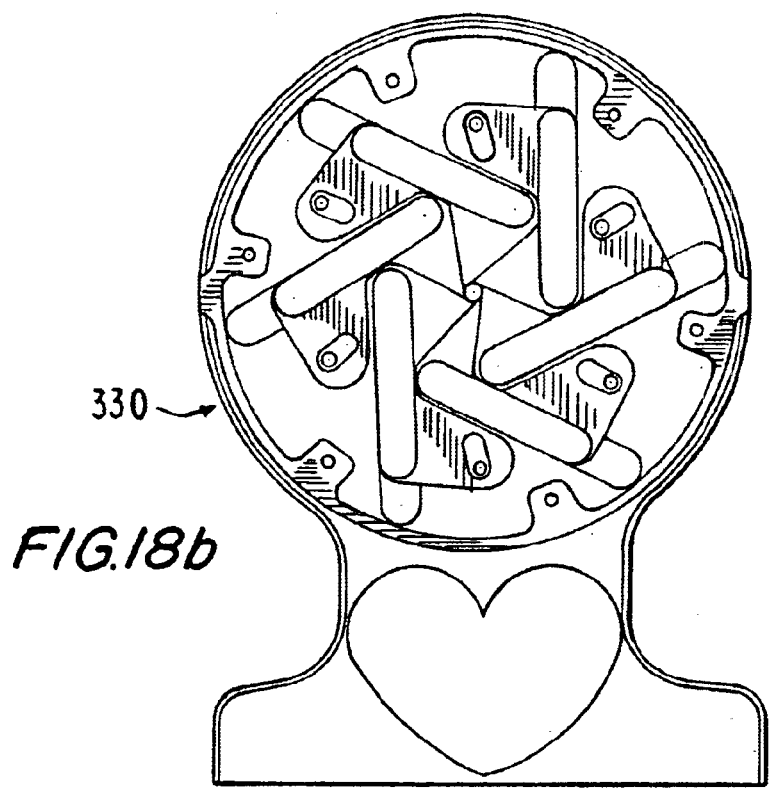
FIGS. 18a and 18b demonstrate a crimping device according to the present invention, which can crimp a valve device in the operating theater as part of the implantation procedure.
Figure 18A:
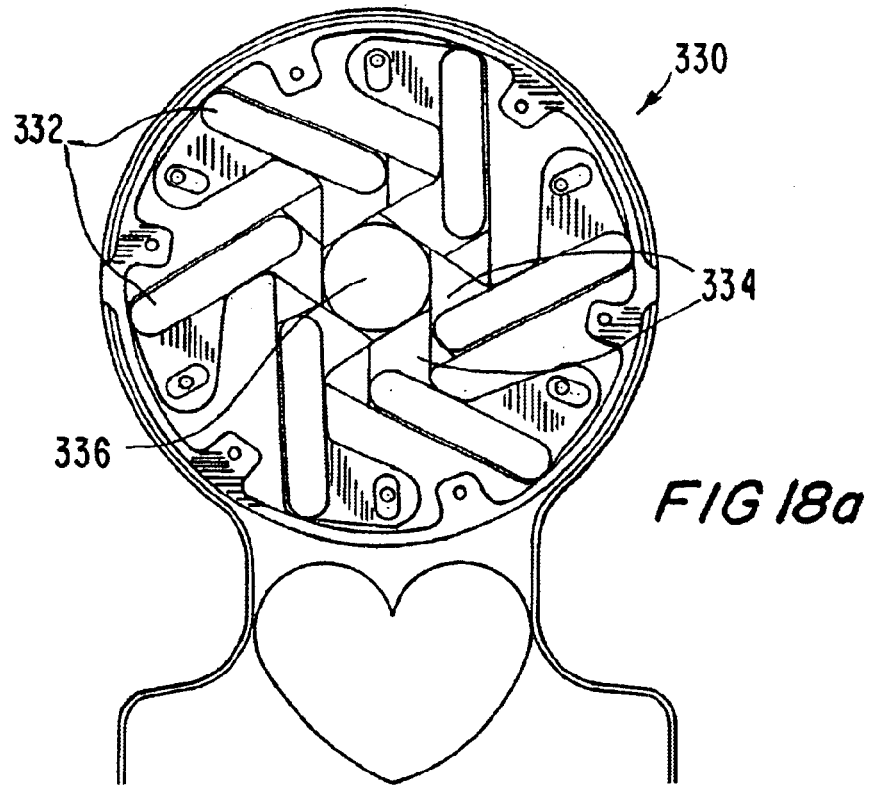

FIGS. 18a and 18b illustrate an accessory crimping device that is adapted to crimp a valve device in the operating theater as part of the implantation procedure. The crimping device 330 comprises several adjustable plates that resemble a typical SLR camera variable restrictor. It is comprised of simultaneously movable plates 332 each provided with a blade 334, that are equally dispersed in a radial symmetry but each plate moves along a line passing off an opening in the center, all plates equidistant from that center opening 336. Initially (see FIG. 18a) the plates are drawn apart providing a large enough opening for the implantable valve to be positioned within that opening. When the plates are drawn towards the center (see FIG. 18b), the opening 336 reduces in size but still retains the annular shape, and this facilitates the crimping of the valve frame to a small dimension suitable for percutaneous positioning.

Figure 19A:
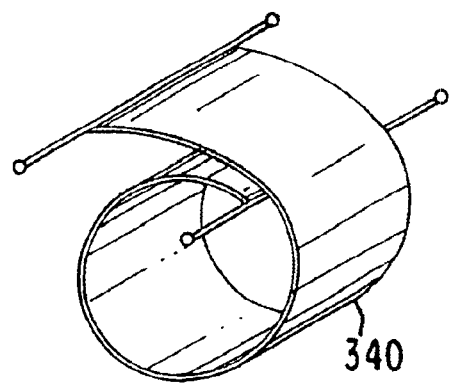
FIGS. 19a to 19c depict a crimping machine according to the present invention, similar to the one described in FIG. 18 with a different mechanical method.
Figure 19B:
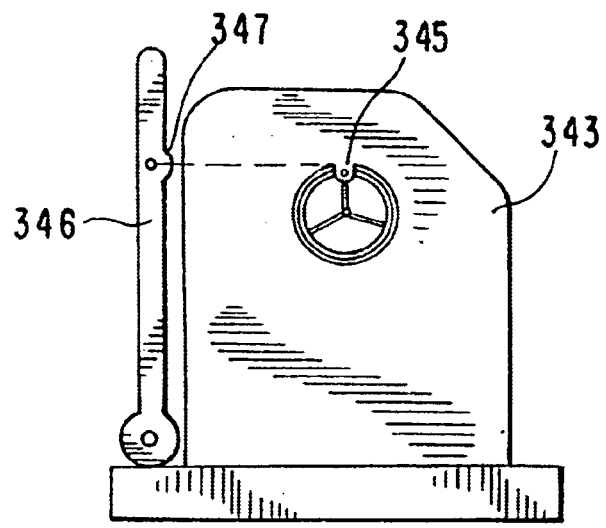
Figure 19C:
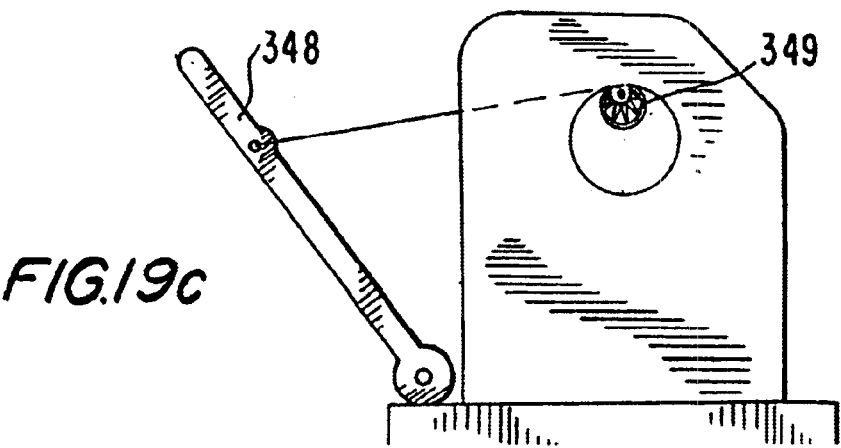

FIG. 19a depicts a crimping method for the support stent of the valve prosthesis device of the present invention, whereby stent 340 is curled. In FIG. 19b a crimping device 343 is shown, comprising a body having an annular void in which an expanded stent is positioned. Lever 346 is connected to the end 347 of the stent and as the lever is pulled the stent is curled about axle 345 into a curled position 349 (FIG. 19c).

Figure 20A:
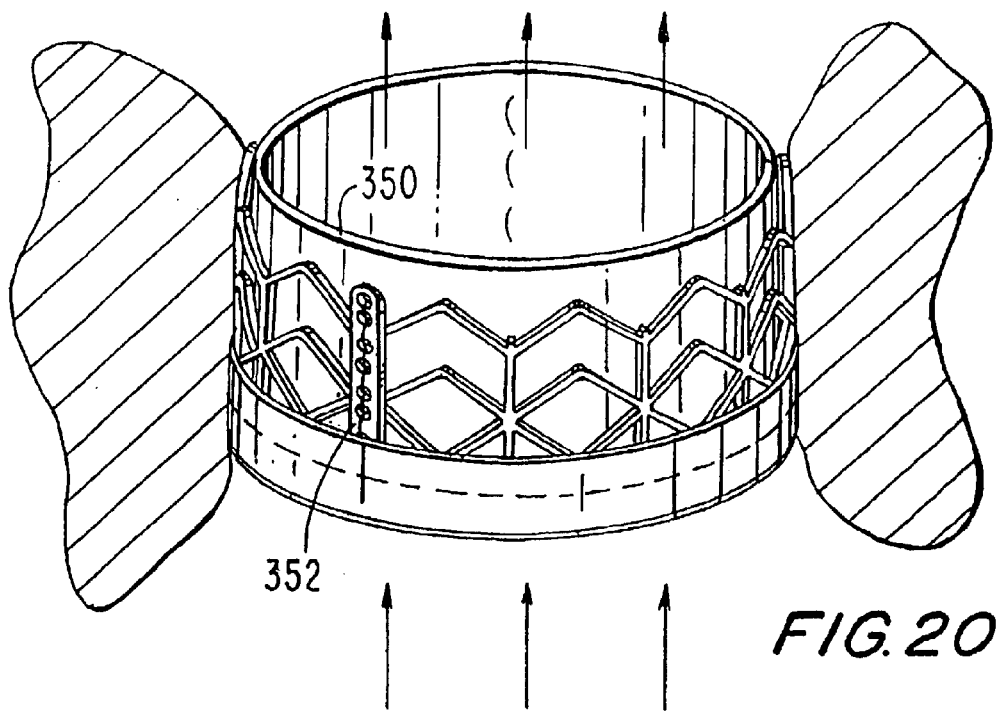
FIGS. 20a and 20b demonstrate a valve according to the present invention, made of a tube mounted on a stent. During systole the tube is fully open and during diastole the tube collapses according to the mounting geometry providing tight sealing.
Figure 20B:
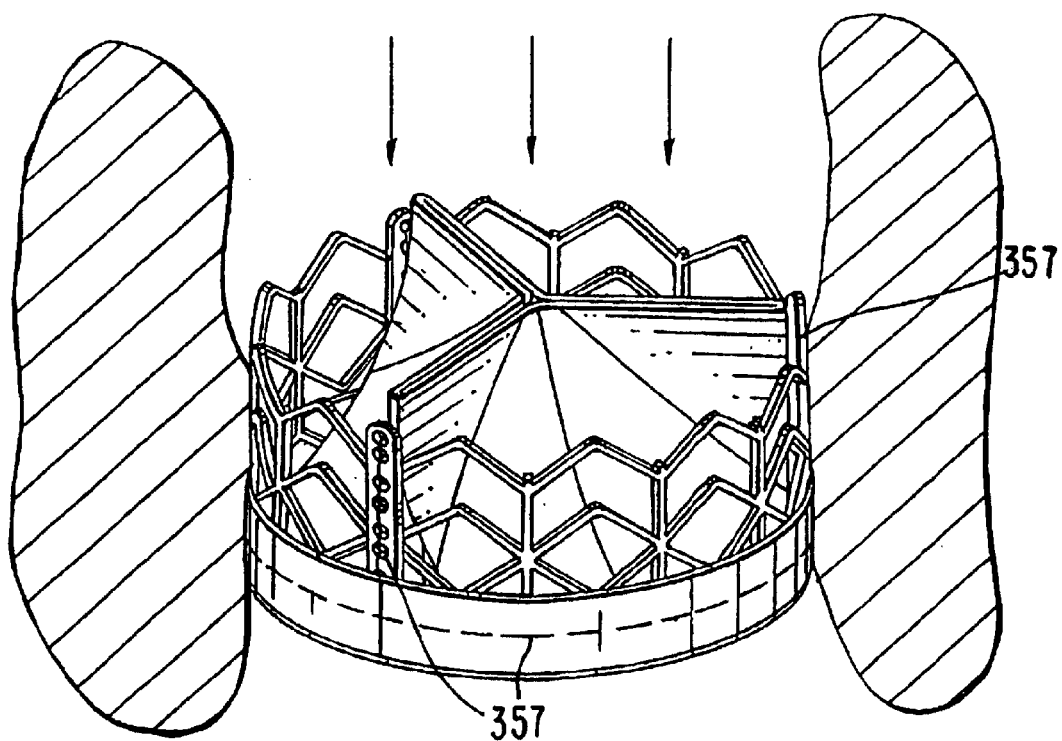

FIGS. 20a and 20b depict a valve made of a simple tube mounted to a stent 352. During systole period the tube is fully open and during diastole period the tube collapses according to the mounting geometry 357 and achieves sealing.

Figure 21:
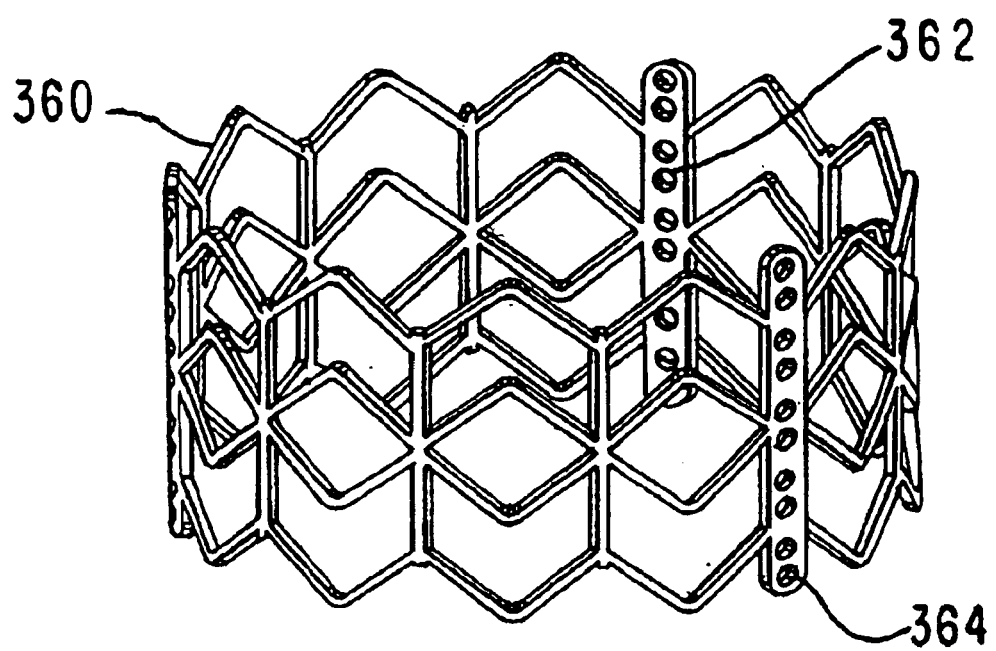
FIG. 21 depicts a stent structure according to the present invention, with built-in mounting portions of constant length, which allow valve mounting.

FIG. 21 describes a newly designed support stent 360 in its open position. Three of the longitudinal struts 362 are full and thick and always stay with their original constant size, serving as anchoring support. Each of these struts 362 is provided with a plurality of bores 364, which are later used for mounting the valve assembly (not shown) and tying it to stent 360. Between struts 362 a web-like construction is provided, which is capable of being crimped to a narrow state and capable of being deployed again to a wider state.

Figure 22:
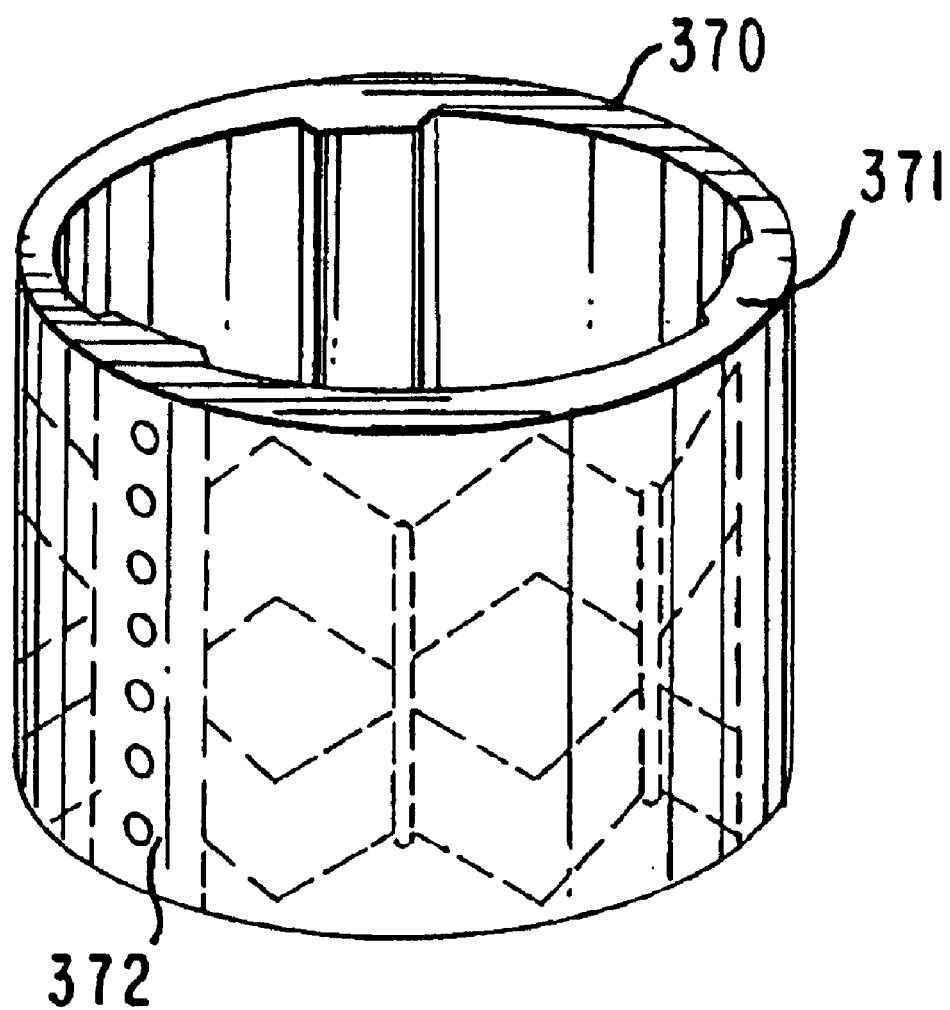
FIG. 22 depicts yet another preferred embodiment a valve assembly in accordance with the present invention, having dilated supports.

FIG. 22 illustrates another preferred embodiment of an implantable prosthetic valve according to the present invention. It comprises a metal tube 370, having three portions with a thicker wall 371 than in the rest of the tube 370, these areas form the longitudinal columns 372 in the construction, after the tube is cut to its final form. The advantage of such a construction is in its superior bending strength, in specific required portions of the construction, with minimal interference to the crimped volume of the whole construction.

Figure 23A:
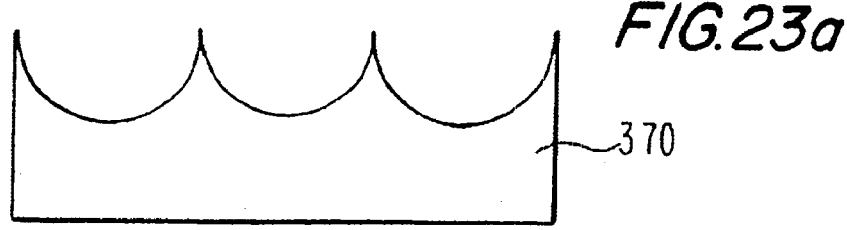
FIGS. 23a to 23e depict stages in a method of manufacturing an implantable prosthetic valve in accordance with another preferred embodiment of the present invention.
Figure 23B:
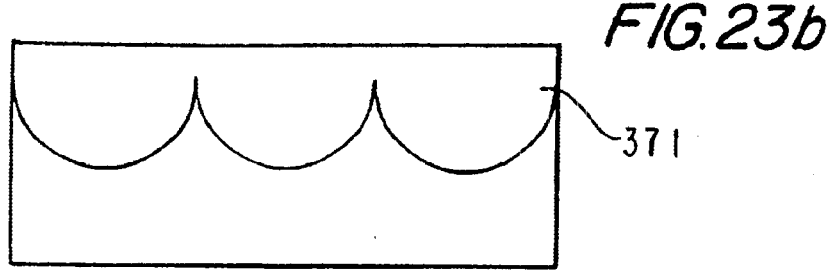
Figure 23C:
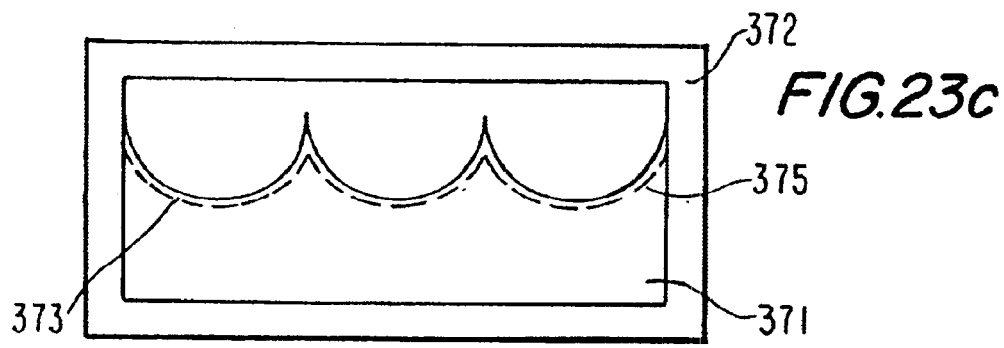
Figure 23D:
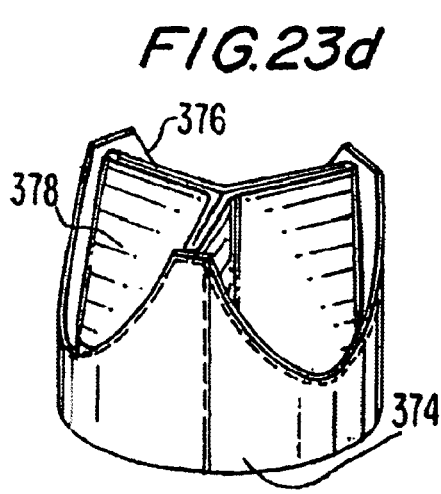
Figure 23E:
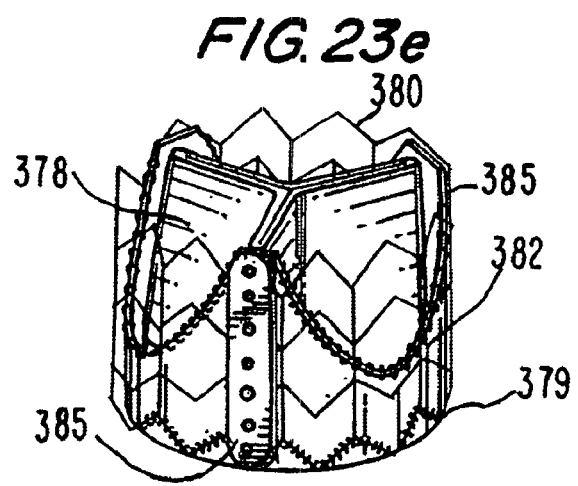

FIGS. 23a to 23c depict a new method of manufacturing an artificial or biological crimpable valve device. A piece of fabric material 370 (FIG. 23a), is dipped in PU to create a portion which is later formed into valve leaflets 371 (FIG. 23b). This composite material 371 is then attached to an additional piece of fabric such as PET 372 by means of stitching, suturing or other attaching technique 373 (FIG. 23c). The resulting fabric 375 is cut along stitching line 373 leaving enough material to later suture the valve assembly to the support construction. It is then formed to a tubular shape and stitched 374 (FIG. 23d). The tubular valve is then attached to a support construction 380 by suturing the bottom part around the valve 379 tightly to prevent leakage, and around the cut fabric line 376 (FIG. 23e). This open wall structure 378 allows blood flow to the coronary arteries. The valve is later placed with the coronary artery between the support columns 385. Additional variations of this can be made by replacing the composite material 371/370 with a biological patch such as a suitable pericardium patch. In some cases it is possible to make the same valve without cutting the fabric 372 with the shaped cut 376, and by that create a valve with an outer tubular shape. The embodiment of FIGS. 23a to 23c is easy to manufacture as it is generally flat throughout most of the production process and only at the final stage of mounting on the support stent is it given a three-dimensional form.

A typical size of an aortic prosthesis valve is from about 19 to about 25 mm in diameter. A maximal size of a catheter inserted into the femoral artery should be no more than 8 mm in diameter. The present invention introduces a device, which has the ability to change its diameter from about 4 mm to about 25 mm. Artificial valves are not new; however, artificial valves in accordance with the present invention posses the ability to change shape and size for the purpose of delivery and as such are novel. These newly designed valves require new manufacturing methods and technical inventions and improvements, some of which were described herein.

As mentioned earlier, the material of which the valve is made from can be either biological or artificial. In any case new technologies are needed to create such a valve.

To attach the valve to the body, the blood vessels determine the size during delivery, and the requirements for it to work efficiently, there is a need to mount it on a collapsible construction which can be crimped to a small size, be expanded to a larger size, and be strong enough to act as a support for the valve function. This construction, which is in somewhat similar to a large "stent", can be made of different materials such as Nitinol, biocompatible stainless steel, polymeric material or a combination of all. Special requirement for the stent are a subject of some of the embodiments discussed herein.

The mounting of the valve onto a collapsible stent is a new field of problems. New solutions to this problem are described herein.

Another major aspect of the design of the valve of the present invention is the attachment to the body.

In the traditional procedure the valve is sutured in place by a complicated suturing procedure. In the case of the percutaneous procedure there is no direct access to the implantation site therefore different attachment techniques are needed.

Another new problem that is dealt herein is the delivery procedure, which is new and unique. Positioning of the device in the body in an accurate location and orientation requires special marking and measuring methods of the device and surgical site as was disclosed herein.

Artificial polymer valves require special treatment and special conditions when kept on a shelf, as well as a special sterilization procedure. One of the consequences of the shelf treatment is the need to crimp the valve during the implantation procedure. A series of devices and inventions to allow the crimping procedure are disclosed herein.

It should be clear that the description of the embodiments and attached Figures set forth in this specification serves only for a better understanding of the invention, without limiting its scope as covered by the following claims.

It should also be clear that a person skilled in the art, after reading the present specification could make adjustments or amendments to the attached Figures and above described embodiments that would still be covered by the following claims.

What is claimed is:

1. A valve prosthesis device suitable for implantation in body ducts, the device comprising:

a support stent, comprised of a deployable construction adapted to be initially crimped in a narrow configuration suitable for catheterization through the body duct to a target location and adapted to be deployed by exerting substantially radial forces from within by means of a deployment device to a deployed state in the target location, the support stent provided with a plurality of longitudinally rigid support beams of fixed length; and a valve assembly comprising a flexible conduit having an inlet end and an outlet, made of pliant material attached to the support beams providing collapsible slack portions of the conduit at the outlet, the valve assembly being rolled over the support stent at the inlet, whereby when flow is allowed to pass through the valve prosthesis device from the inlet to the outlet the valve assembly is kept in an open position, whereas a reverse flow is prevented as the collapsible slack portions of the valve assembly collapse inwardly providing blockage to the reverse flow.

2. The valve device of claim 1, wherein the support stent comprises an annular frame.

3. The valve device of claim 1, wherein said valve assembly has a tricuspid configuration.

4. The valve device of claim 1, wherein said valve assembly is made from biocompatible material.

5. The valve device of claim 4, wherein the valve assembly is made from pericardial tissue, or other biological tissue.

6. The valve device of claim 1, wherein said valve assembly is made from biocompatible polymers.

7. The valve device of claim 6, wherein the valve assembly is made from materials selected from polyurethane and polyethylene terphthalane.

8. The valve device of claim 7, wherein said valve assembly comprises a main body made from polyethylene terphthalane and leaflets made from polyurethane.

9. The valve device of claim 1, wherein said support stent is made from nickel titanium.

10. The valve device of claim 1, wherein the support beams are substantially equidistant and substantially parallel so as to provide anchorage for the valve assembly.

11. The valve device of claim 1, wherein the support beams are provided with bores so as to allow stitching or tying of the valve assembly to the beams.

12. The valve device of claim 1, wherein the support beams are chemically adhered to the support stent.

13. The valve device of claim 1, wherein said valve assembly is riveted to the support beams.

14. The valve device of claim 1, wherein said valve assembly is stitched to the support beams.

15. The valve device of claim 1, wherein said beams are manufactured by injection using a mold, or by machining.

16. The valve device of claim 1, wherein said valve device is manufactured using forging or dipping techniques.

17. The valve device of claim 1, wherein said valve assembly leaflets are longer than needed to exactly close the outlet, thus when they are in the collapsed state substantial portions of the leaflets fall on each other creating better sealing.

18. The valve device of claim 1, wherein said valve assembly is made from a coiled a polymer, coated by a coating layer of same polymer.

19. The valve device of claim 18, wherein said polymer is polyurethane.

20. The valve device of claim 1, wherein the support stent is provided with heavy metal markers so as to enable tracking and determining the valve device position and orientation.

21. The valve device of claim 20, wherein the heavy metal markers are selected from gold, platinum, iridium, or tantalum.

22. The valve device of claim 1, wherein the valve assembly leaflets are provided with radio-opaque material at the outlet, so as to help tracking the valve device operation in vivo.

23. The valve device of claim 22, wherein said radio-opaque material comprises gold thread.

24. The valve device of claim 1, wherein the diameter of said support stent, when fully deployed is in the range of from about 19 to about 25 mm.

25. The valve device of claim 1, wherein the diameter of said support stent may be expanded from about 4 to about 25 mm.

26. The valve device of claim 1, wherein the support beams are provided with bores and wherein the valve assembly is attached to the support beams by means of u-shaped rigid members that are fastened to the valve assembly and that are provided with extruding portions that fit into matching bores on the support beams.

27. The valve device of claim 1, wherein the support beams comprise rigid support beams in the form of frame construction, and the valve assembly pliant material is inserted through a gap in the frame and a fastening rod is inserted through a pocket formed between the pliant material and the frame and holds the valve in position.

28. A valve prosthesis device suitable for implantation in body ducts, the device comprising:

a support stent, comprised of a deployable construction adapted to be initially crimped in a narrow configuration suitable for catheterization through the body duct to a target location and adapted to be deployed by exerting substantially radial forces from within by means of a deployment device to a deployed state in the target location, the support stent provided with a plurality of longitudinally rigid support beams of fixed length; and a valve assembly comprising a flexible conduit having an inlet end and an outlet, made of pliant material attached to the support beams providing collapsible slack portions of the conduit at the outlet, wherein the valve assembly is made from coiled wire coated with coating material.

29. The valve device of claim 28, wherein the coiled wire coating material is made from polyurethane.

30. The valve device of claim 1, wherein a strengthening wire is interlaced in the valve assembly at the outlet of the conduit so as to define a fault line about which the collapsible slack portion of the valve assembly may flap.

31. The valve device of claim 30, wherein the strengthening-wire is made from nickel titanium alloy.

* * * * *